(12) United States Patent
Hitko et al.

(10) Patent No.: US 10,976,312 B2
(45) Date of Patent: *Apr. 13, 2021

(54) COMPOSITIONS AND METHODS FOR CAPTURE OF CELLULAR TARGETS OF BIOACTIVE AGENTS

(71) Applicant: Promega Corporation, Madison, WI (US)

(72) Inventors: Carolyn W. Hitko, Grover Beach, CA (US); Robin Hurst, Madison, WI (US); Thomas Kirkland, Atascadero, CA (US); Dieter Klaubert, Arroyo Grande, CA (US); Poncho Meisenheimer, San Luis Obispo, CA (US); Nidhi Nath, Madison, WI (US); Rachel Friedman Ohana, Madison, WI (US); Paul Otto, Madison, WI (US); Marjeta Urh, Madison, WI (US); Harry Tetsuo Uyeda, Los Osos, CA (US); Keith Wood, Mt. Horeb, WI (US); Ji Zhu, Croton on Hudson, NY (US)

(73) Assignee: Promega Corporation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/402,879

(22) Filed: Jan. 10, 2017

(65) Prior Publication Data

US 2017/0115283 A1 Apr. 27, 2017

Related U.S. Application Data

(63) Continuation of application No. 14/104,814, filed on Dec. 12, 2013, now Pat. No. 9,551,705.

(60) Provisional application No. 61/788,313, filed on Mar. 15, 2013, provisional application No. 61/736,426, filed on Dec. 12, 2012.

(51) Int. Cl.
*G01N 33/543* (2006.01)

(52) U.S. Cl.
CPC . *G01N 33/54333* (2013.01); *G01N 33/54306* (2013.01); *G01N 33/54326* (2013.01)

(58) Field of Classification Search
CPC ....... G01N 33/54306; G01N 33/54326; G01N 33/54333
See application file for complete search history.

(56) References Cited

U.S. PATENT DOCUMENTS

| 5,344,926 | A | 9/1994 | Murakata et al. |
|---|---|---|---|
| 7,425,436 | B2 | 9/2008 | Darzins et al. |
| 7,429,472 | B2 | 9/2008 | Darzins et al. |
| 7,829,531 | B2 | 11/2010 | Sener et al. |
| 7,867,726 | B2 | 1/2011 | Wood et al. |
| 7,888,086 | B2 | 2/2011 | Darzins et al. |
| 7,935,803 | B2 | 5/2011 | Darzins et al. |
| RE42,931 | E | 11/2011 | Wood et al. |
| 8,168,405 | B2 | 5/2012 | Darzins et al. |
| 8,202,700 | B2 | 6/2012 | Darzins et al. |
| 8,257,939 | B2 | 9/2012 | Wood et al. |
| 8,557,970 | B2 | 10/2013 | Encell et al. |
| 8,669,103 | B2 | 3/2014 | Binkowski et al. |
| 9,551,705 | B2 * | 1/2017 | Hitko ............... G01N 33/54326 |
| 10,168,323 | B2 * | 1/2019 | Hitko ............... G01N 33/543 |
| 2006/0024808 | A1 | 2/2006 | Darzins et al. |
| 2006/0276586 | A1 | 12/2006 | Kim et al. |
| 2010/0281552 | A1 | 11/2010 | Encell et al. |
| 2014/0199712 | A1 | 7/2014 | Hitko et al. |
| 2014/0287427 | A1 | 9/2014 | Hitko et al. |
| 2014/0322738 | A1 | 10/2014 | Hitko et al. |
| 2016/0355523 | A1 * | 12/2016 | Levin ............... C07D 491/22 |

FOREIGN PATENT DOCUMENTS

| JP | 2009-296973 | 12/2009 |
|---|---|---|
| WO | WO 1993/06868 | 4/1993 |
| WO | WO 1994/08629 | 4/1994 |
| WO | WO 1994/09056 | 4/1994 |
| WO | WO 1996/26754 | 9/1994 |
| WO | WO 2010/053249 | 5/2010 |
| WO | WO 2012/061529 | 5/2012 |
| WO | WO 2014/093671 | 7/2014 |

OTHER PUBLICATIONS

Ohana et al., "Deciphering the Cellular Targets of Bioactive Compounds Using a Chloroalkane Capture Tag," ACS Chem. Biol., 2015, vol. 10, No. 10, pp. 2316-2324.*
Encell et al., "Development of a dehalogenase-based protein fusion tag capable of rapid, selective and covalent attachment to customizable ligands," Curr. Chem. Genomics, 2012, 6, (suppl 1-M7) pp. 55-71.*
Shin et al., "Blocking Tumor Cell Migration and Invasion with Biphenyl Isoxazole Derivative KRIBB3, a Synthetic Molecule That Inhibits Hsp27 Phosphorylation," J. Biol. Chem., 2005, vol. 280, No. 50, pp. 41439-41448.*
Leslie et al., "Identification of the cellular targets of bioactive small organic molecules using affinity reagents," Chem. Soc. Rev., 2008, vol. 37, No. 7, pp. 1347-1360.*
Godl et al., An efficient proteomics method to identify the cellular targets of protein kinase inhibitors, PNAS, 2003, 100:15434-15439.
Gutterman, Covalent Drugs Form Long-Lived Ties, Chemical and Engineering News, 2011, 89:19-26.
Hong et al., HaloTag: a novel reporter gene for positron emission tomography, Am J Transl Res, 2011, 3:392-403.
International Search Report and Written Opinion for PCT/US2013/074756, dated May 2, 2014, 21 pages.

(Continued)

*Primary Examiner* — Galina M. Yakovleva
(74) *Attorney, Agent, or Firm* — Casimir Jones SC; David W. Staple

(57) ABSTRACT

The present invention provides compositions and methods for capture and identification of the cellular targets of a bioactive agent. In particular, provided herein are bioactive agents tethered to capture ligand, cellular targets (optionally tagged with a reporter), capture proteins (optionally present as capture fusions), surfaces (e.g., displaying, capture ligands, capture proteins, or capture fusions), and methods of capturing and identifying the cellular targets of a bioactive agent therewith.

8 Claims, 20 Drawing Sheets

Specification includes a Sequence Listing.

(56) References Cited

OTHER PUBLICATIONS

Kwok et al. The anti-inflammatory natural product parthenolide from the medicinal herb Feverfew directly binds to and inhibits IkappaB kinase. Chem Biol. Aug. 2001;8(8):759-66.
Los et al., HaloTag: a novel protein labeling technology for cell imaging and protein analysis. ACS Chem Biol. Jun. 20, 2008;3(6):373-82.
Salisbury et al., Optimization of activity-based probes for proteomic profiling of histone deacetylase complexes, J Am Chem Soc, 2008, 130:2184-2194.
Schaefer et al., Phenylalanine-containing hydroxamic acids as selective inhibitors of class IIb histone deacetylases (HDACs), Bioorg Med Chem, 2008, 16:2011-2033.
Tecle et al, The Design, Synthesis and Potential Utility of Fluorescence Probes that Target DFG-out Conformation of p38α for High Throughput Screening Binding Assay, Chem Biol Drug Des, 2009, 74:547-549.
Tomalia et al. Starburs Dendrimers: Molecular-Level Control of Size, Shape, Surface Chemistry, Topology, and Flexibility from Atoms to Macroscopic Matter. Angew. Chem. Int. Ed. Engl. 1990;29:138-175.
Wittich et al., Structure-activity relationships on phenylalanine-containing inhibitors of histone deacetylase: in vitro enzyme inhibition, induction of differentiation, and inhibition of proliferation in Friend leukemic cells, J. Med. Chem., 2002, 45:3296-3309.
Barrios-Rodiles et al., High-Throughput Mapping of a Dynamic Signaling Network in Mammalian Cells. Science. 2005;307:1621-5.
Sato et al., Biochemical target isolation for novices: affinity-based strategies, Chem Biol, 2010, 17:616-623.

\* cited by examiner

FIG. 8B

| Identified Proteins (6) | MW (kDa) | MTX-CA (SPC) | control (SpC) | MTX-CA NSAF | control NSAF |
|---|---|---|---|---|---|
| Dihydrofolate reductase OS=Homo sapiens GN=DHFR PE=1 SV=2 | 21 | 77 | 0 | 0.189840 | 0 |
| Peroxiredoxin-2 OS=Homo sapiens GN=PRDX2 PE=1 SV=5 | 22 | 11 | 0 | 0.025901 | 0 |
| Serpin B12 OS=Homo sapiens GN=SERPINB12 PE=1 SV=1 | 46 | 7 | 2 | 0.007883 | 0.011849 |
| Collagen alpha-1(I) chain OS=Homo sapiens GN=COL1A1 PE=1 SV=5 | 139 | 9 | 0 | 0.003334 | 0 |
| Collagen alpha-2(I) chain OS=Homo sapiens GN=COL1A2 PE=1 SV=7 | 129 | 8 | 0 | 0.003213 | 0 |
| Myosin-9 OS=Homo sapiens GN=MYH9 PE=1 SV=4 | 227 | 13 | 0 | 0.002967 | 0 |

In bold Known targets of Methotrexate including DHFR

FIG. 9B

| Identified Proteins (23) | MW (kDa) | BIRB-CA (SPC) | control (SpC) | BIRB-CA NSAF | control NSAF |
|---|---|---|---|---|---|
| 10 kDa heat shock protein, mitochondrial OS=Homo sapiens GN=HSPE1 PE=1 SV=2 | 11 | 7 | 0 | 0.022362 | 0 |
| 14-3-3 protein epsilon OS=Homo sapiens GN=YWHAE PE=1 SV=1 | 29 | 8 | 0 | 0.009694 | 0 |
| L-lactate dehydrogenase B chain OS=Homo sapiens GN=LDHB PE=1 SV=2 | 37 | 10 | 0 | 0.009497 | 0 |
| Alpha-enolase OS=Homo sapiens GN=ENO1 PE=1 SV=2 | 47 | 12 | 0 | 0.008972 | 0 |
| Mitogen-activated protein kinase 14 OS=Homo sapiens GN=MAPK14 PE=1 SV=3 | 41 | 10 | 0 | 0.008571 | 0 |
| Probable ATP-dependent RNA helicase DDX17 OS=Homo sapiens GN=DDX17 PE=1 SV=1 | 72 | 17 | 0 | 0.008297 | 0 |
| Prohibitin OS=Homo sapiens GN=PHB PE=1 SV=1 | 30 | 6 | 0 | 0.007028 | 0 |
| 60 kDa heat shock protein, mitochondrial OS=Homo sapiens GN=HSPD1 PE=1 SV=2 | 61 | 12 | 2 | 0.006913 | 0.001685 |
| L-lactate dehydrogenase A chain OS=Homo sapiens GN=LDHA PE=1 SV=2 | 37 | 7 | 0 | 0.006648 | 0 |
| Fructose-bisphosphate aldolase A OS=Homo sapiens GN=ALDOA PE=1 SV=2 | 39 | 7 | 0 | 0.006307 | 0 |
| 14-3-3 protein gamma OS=Homo sapiens GN=YWHAG PE=1 SV=2 | 28 | 5 | 0 | 0.006275 | 0 |
| Heat shock protein HSP 90-beta OS=Homo sapiens GN=HSP90AB1 PE=1 SV=4 | 83 | 13 | 0 | 0.005504 | 0 |
| D-3-phosphoglycerate dehydrogenase OS=Homo sapiens GN=PHGDH PE=1 SV=4 | 57 | 8 | 0 | 0.004932 | 0 |
| Tubulin beta chain OS=Homo sapiens GN=TUBB PE=1 SV=2 | 50 | 7 | 0 | 0.004920 | 0 |
| Heat shock protein HSP 90-alpha OS=Homo sapiens GN=HSP90AA1 PE=1 SV=5 | 85 | 11 | 0 | 0.004548 | 0 |
| Cyclin-dependent kinase 8 OS=Homo sapiens GN=CDK8 PE=1 SV=1 | 53 | 5 | 0 | 0.003315 | 0 |
| Protein-glutamine gamma-glutamyltransferase E OS=Homo sapiens GN=TGM3 PE=1 SV | 77 | 7 | 0 | 0.003195 | 0 |
| Protein enabled homolog OS=Homo sapiens GN=ENAH PE=1 SV=2 | 67 | 6 | 0 | 0.003147 | 0 |
| T-complex protein 1 subunit eta OS=Homo sapiens GN=CCT7 PE=1 SV=2 | 59 | 5 | 0 | 0.002978 | 0 |
| ATP-dependent RNA helicase A OS=Homo sapiens GN=DHX9 PE=1 SV=4 | 141 | 9 | 0 | 0.002243 | 0 |
| Protein Shroom3 OS=Homo sapiens GN=SHROOM3 PE=1 SV=2 | 217 | 11 | 0 | 0.001781 | 0 |
| Myosin-9 OS=Homo sapiens GN=MYH9 PE=1 SV=4 | 227 | 11 | 0 | 0.001703 | 0 |
| FACT complex subunit SPT16 OS=Homo sapiens GN=SUPT16H PE=1 SV=1 | 120 | 5 | 0 | 0.001464 | 0 |
| STE20-like serine/threonine-protein kinase OS=Homo sapiens GN=SLK PE=1 SV=1 | 143 | 3 | 0 | 0.000073721 | 0 |

In red Known targets of BRIB796 including p38alpha =MAPK14

Mass spec analysis of pull down from HEK293 cells

| Interactors | Mean SpC | | Mean NSAF | | Ratio |
|---|---|---|---|---|---|
| | control | PBI 5040 | control | PBI 5040 | PBI 5040/control |
| HDAC1 | 3.0 | 160.7 | 0.0003 | 0.0204 | 62.5 |
| HDAC2 | 0.0 | 110.3 | 0.0000 | 0.0142 | |
| PARK7 | 0.0 | 27.3 | 0.0000 | 0.0091 | |
| ADO | 0.0 | 16.7 | 0.0000 | 0.0041 | |
| HDAC6 | 0.0 | 78.3 | 0.0000 | 0.0040 | |
| GLO1 | 0.7 | 6.7 | 0.0004 | 0.0022 | 5.0 |
| ENO1 | 3.0 | 16.3 | 0.0004 | 0.0021 | 5.5 |
| LDHB | 2.3 | 8.3 | 0.0003 | 0.0016 | 4.6 |
| HAGH | 0.0 | 8.7 | 0.0000 | 0.0015 | |
| HDAC3 | 0.0 | 8.7 | 0.0000 | 0.0014 | |
| HDAC8 | 0.0 | 8.7 | 0.0000 | 0.0014 | |
| CPPED1 | 0.0 | 6.7 | 0.0000 | 0.0014 | |
| CRKL | 1.3 | 5.3 | 0.0002 | 0.0011 | 5.2 |
| FARSB | 2.3 | 9.0 | 0.0002 | 0.0010 | 4.4 |

- In bold all known direct targets of SAHA
- Results rare represented as the mean of 3 replicate pull down experiments

SEQUENCE LISTING

<160> NUMBER OF SEQ ID NOS: 4

<210> SEQ ID NO 1
<211> LENGTH: 297
<212> TYPE: PRT
<213> ORGANISM: Artificial Sequence
<220> FEATURE:
<223> OTHER INFORMATION: Synthetic

<400> SEQUENCE: 1

```
Met Ala Glu Ile Gly Thr Gly Phe Pro Phe Asp Pro His Tyr Val Glu
1               5                   10                  15

Val Leu Gly Glu Arg Met His Tyr Val Asp Val Gly Pro Arg Asp Gly
            20                  25                  30

Thr Pro Val Leu Phe Leu His Gly Asn Pro Thr Ser Ser Tyr Val Trp
        35                  40                  45

Arg Asn Ile Ile Pro His Val Ala Pro Thr His Arg Cys Ile Ala Pro
    50                  55                  60

Asp Leu Ile Gly Met Gly Lys Ser Asp Lys Pro Asp Leu Gly Tyr Phe
65                  70                  75                  80

Phe Asp Asp His Val Arg Phe Met Asp Ala Phe Ile Glu Ala Leu Gly
                85                  90                  95

Leu Glu Glu Val Val Leu Val Ile His Asp Trp Gly Ser Ala Leu Gly
            100                 105                 110

Phe His Trp Ala Lys Arg Asn Pro Glu Arg Val Lys Gly Ile Ala Phe
        115                 120                 125

Met Glu Phe Ile Arg Pro Ile Pro Thr Trp Asp Glu Trp Pro Glu Phe
    130                 135                 140

Ala Arg Glu Thr Phe Gln Ala Phe Arg Thr Thr Asp Val Gly Arg Lys
145                 150                 155                 160

Leu Ile Ile Asp Gln Asn Val Phe Ile Glu Gly Thr Leu Pro Met Gly
                165                 170                 175

Val Val Arg Pro Leu Thr Glu Val Glu Met Asp His Tyr Arg Glu Pro
            180                 185                 190

Phe Leu Asn Pro Val Asp Arg Glu Pro Leu Trp Arg Phe Pro Asn Glu
        195                 200                 205

Leu Pro Ile Ala Gly Glu Pro Ala Asn Ile Val Ala Leu Val Glu Glu
```

```
               210                 215                 220
Tyr Met Asp Trp Leu His Gln Ser Pro Val Pro Lys Leu Leu Phe Trp
225                 230                 235                 240

Gly Thr Pro Gly Val Leu Ile Pro Pro Ala Glu Ala Ala Arg Leu Ala
                245                 250                 255

Lys Ser Leu Pro Asn Cys Lys Ala Val Asp Ile Gly Pro Gly Leu Asn
                260                 265                 270

Leu Leu Gln Glu Asp Asn Pro Asp Leu Ile Gly Ser Glu Ile Ala Arg
            275                 280                 285

Trp Leu Ser Thr Leu Glu Ile Ser Gly
        290                 295

<210> SEQ ID NO 2
<211> LENGTH: 891
<212> TYPE: DNA
<213> ORGANISM: Artificial Sequence
<220> FEATURE:
<223> OTHER INFORMATION: Synthetic

<400> SEQUENCE: 2
atggcagaaa tcggtactgg ctttccattc gaccccatt atgtggaagt cctgggcgag      60
cgcatgcact acgtcgatgt tggtccgcgc gatggcaccc ctgtgctgtt cctgcacggt    120
aacccgacct cctcctacgt gtggcgcaac atcatcccgc atgttgcacc gacccatcgc    180
tgcattgctc cagacctgat cggtatgggc aaatccgaca accagacctg ggttatttc     240 ttcgacgacc acgtccgctt catggatgcc ttcatcgaag ccctgggtct ggaagaggtc    300
gtcctggtca ttcacgactg ggctccgct ctgggtttcc actgggccaa gcgcaatcca     360
gagcgcgtca aggtattgc atttatggag ttcatccgcc ctatcccgac ctgggacgaa     420
tggccagaat ttgcccgcga gaccttccag gccttccgca ccaccgacgt cggccgcaag    480
ctgatcatcg atcagaacgt ttttatcgag ggtacgctgc cgatgggtgt cgtccgcccg    540
ctgactgaag tcgagatgga ccattaccgc gagccgttcc tgaatcctgt tgaccgcgag    600
ccactgtggc gcttcccaaa cgagctgcca atcgccggtg agccagcgaa catcgtcgcg    660
ctggtcgaag aatacatgga ctggctgcac cagtcccctg tcccgaagct gctgttctgg    720
ggcaccccag gcgttctgat cccaccggcc gaagccgctc gcctggccaa agcctgcct    780 aactgcaagg ctgtggacat cggcccgggt ctgaatctgc tgcaagaaga caaccggac     840 ctgatcggca gcgagatcgc gcgctggctg tcgacgctcg agatttccgg c             891

<210> SEQ ID NO 3
<211> LENGTH: 169
<212> TYPE: PRT
<213> ORGANISM: Oplophorus gracilirostris

<400> SEQUENCE: 3

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
                20                  25                  30

Ala Leu Gly Val Ser Val Thr Pro Ile Gln Lys Val Val Leu Ser Gly
            35                  40                  45

Glu Asn Gly Leu Lys Ala Asp Ile His Val Ile Ile Pro Tyr Glu Gly
        50                  55                  60

Leu Ser Gly Phe Gln Met Gly Leu Ile Glu Met Ile Phe Lys Val Val
65                  70                  75                  80
```

```
Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 4
<211> LENGTH: 513
<212> TYPE: DNA
<213> ORGANISM: Artificial Sequence
<220> FEATURE:
<223> OTHER INFORMATION: Synthetic

<400> SEQUENCE: 4
atggtgttta ccttggcaga tttcgttgga gactggcaac agacagctgg atacaaccaa      60
gatcaagtgt tagaacaagg aggattgtct agtctgttcc aagccctggg agtgtcagtc     120
accccaatcc agaaagttgt gctgtctggg gagaatgggt aaaagctga tattcatgtc      180 atcatccctt acgagggact cagtggtttt caaatgggtc tgattgaaat gatcttcaaa     240
gttgtttacc cagtggatga tcatcatttc aagattattc tccattatgg tacactcgtt     300
attgacggtg tgacaccaaa catgattgac tactttggac gcccttaccc tggaattgct     360
gtgtttgacg gcaagcagat cacagttact ggaactctgt ggaacggcaa caagatctat     420
gatgagcgcc tgatcaaccc agatggttca ctcctcttcc gcgttactat caatggagtc     480
accggatggc gctttgcga gaacattctt gcc                                   513
```

COMPOSITIONS AND METHODS FOR CAPTURE OF CELLULAR TARGETS OF BIOACTIVE AGENTS

CROSS-REFERENCE TO RELATED APPLICATIONS

The present application is a continuation of U.S. patent application Ser. No. 14/104,814, filed Dec. 12, 2013, now allowed, which claims priority to U.S. Provisional Patent Application Ser. No. 61/736,426 filed Dec. 12, 2012; and U.S. Provisional Patent Application Ser. No. 61/883,313 filed Sep. 19, 2013; both of which are hereby incorporated by reference in their entireties.

FIELD

The present invention provides compositions and methods for capture and identification of the cellular targets of a bioactive agent. In particular, provided herein are bioactive agents tethered to capture ligand, cellular targets (endogenous or optionally tagged with a reporter), capture proteins (optionally present as capture fusions), surfaces (e.g., displaying capture ligands, capture proteins, or capture fusions), and methods of capturing and identifying the cellular targets of a bioactive agent therewith.

BACKGROUND

Cell-based phenotypic screening is increasingly being used for discovery of bioactive drug candidates. The targets of drug candidates naturally operate within a cellular context, and how they interact with bioactive molecules (e.g., synthetic molecules) is significantly influenced by this context. For this reason, when trying to identify unknown targets to bioactive molecules, it is preferable to allow the target to bind to the bioactive molecules within a living cell, before being captured for identification. Thus, methods that allow binding to occur in cell lysates before capture are not as preferred. This is true for the primary targets that mediate the desired
bioactivity, and for off targets that may result in liabilities or interferences. Discovering and validating protein targets for such bioactive molecules often uses a combination of affinity enrichment and mass spectrometry methods. Such methods face several challenges. First, the often moderate to weak binding between a target molecule and a protein target makes it hard to capture a target protein or protein complexes or biases the results towards high affinity interactors. Moreover, affinity enrichment methods typically use a solid support immobilized with the candidate target molecule. The kinetics of binding on solid surfaces are much slower when compared to solution-based kinetics, further decreasing the chance of capturing a target protein or protein complexes. Non-specific binding of proteins from cell lysate to the solid support results in high background that further complicates the identification of the cellular target using mass spectrometry (MS). Such methods often result in a large number of putative hits, making it necessary to run secondary screens to validate the potential targets. High-throughput validation assays for target molecule-protein interactions require further development and optimization making it resource intensive process.

SUMMARY

In some embodiments, the present invention provides compositions and systems (e.g., cells, reaction mixture, kit, container, etc.) comprising one or more (e.g., all) of: (a) a cellular target of a bioactive agent; (b) a fusion of a first capture protein and a second capture protein; (c) the bioactive agent tethered to a first capture ligand, wherein the first capture ligand forms a covalent bond with the first capture protein upon interaction thereof and (d) a solid surface displaying a second capture ligand, wherein the second capture ligand forms a covalent bond with the second capture protein upon interaction thereof. In some embodiments, (a) comprises a plurality of cellular targets of a bioactive compound. In some embodiments, the cellular target is expressed intracellularly as a fusion with a reporter. In some embodiments, the reporter is a bioluminescent reporter. In some embodiments, the reporter is a portion, component, or subunit of a bioluminescent protein. In some embodiments, the bioluminescent reporter comprises a polypeptide with at least 70% sequence identity with SEQ ID NO.: 3 (e.g., 75%, 80%, 85%, 90%, 95%, 98%, 99%). In some embodiments, the first and second capture proteins both comprise at least 70% sequence identity with SEQ ID NO.: 1 (e.g., 75%, 80%, 85%, 90%, 95%, 98%, 99%). In some embodiments, the fusion is a homodimer. In some embodiments, the bioactive agent is a small molecule. In some embodiments, the cellular target is a binding partner of the bioactive agent. In some embodiments, the cellular target comprises a combination of molecules, such as a complex of two or more proteins, or proteins and nucleic acids. In some embodiments, the first capture ligand and second capture ligand comprise the same molecular structure. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, a solid surface is magnetic. In some embodiments, a solid surface is non-magnetic. In some embodiments, the cellular target is bound to the bioactive agent, the first capture protein is bound to the first capture ligand, and the second capture protein is bound to the second capture ligand on the solid surface.

In certain embodiments, the present invention provides methods of capturing the cellular target comprising the steps of: (a) administering a bioactive agent tethered to a first capture ligand to a cell comprising a cellular target of the bioactive agent under conditions such that the cellular target binds the bioactive agent; (b) lysing the cell to produce a cell lysate; (c) contacting the cell lysate with a fusion of a first capture protein and a second capture protein under conditions in which the first capture ligand forms a covalent bond with the first capture protein; (d) contacting the cell lysate with a solid surface displaying a second capture ligand under conditions in which the first capture ligand forms a covalent bond with the first capture protein; and (e) separating the solid surface from the cell lysate. In other embodiments, the present invention provides methods of capturing the cellular target comprising the steps of: (a) administering a bioactive agent tethered to a first capture ligand to a cell comprising a cellular target of the bioactive agent under conditions such that the cellular target binds the bioactive agent; (b) lysing the cell to produce a cell lysate; (c) contacting the cell lysate with a solid surface displaying a second capture ligand bound to a fusion of a first capture protein and a second capture protein, wherein the second capture protein and the second capture ligand are covalently bound; and (d) separating the solid surface from the cell lysate. In some embodiments, the cellular target is endogenous to a cell. In some embodiments, the cellular target is a fusion with a reporter.

In certain embodiments, the present invention provides methods of capturing the cellular target comprising the steps of: (a) administering a bioactive agent tethered to a first capture ligand to a cell comprising a cellular target of the bioactive agent under conditions such that the cellular target binds the bioactive agent; (b) contacting the first capture ligand with a fusion of a first capture protein and a second capture protein under conditions in which the first capture ligand forms a covalent bond with the first capture protein; (c) contacting the capture fusion with a solid surface displaying a second capture ligand under conditions in which the first capture ligand forms a covalent bond with the first capture protein; and (d) separating the solid surface from the cell lysate. In some embodiments, methods comprise a step of lysing the cell to form a lysate. In other embodiments, the present invention provides methods of capturing the cellular target comprising the steps of: (a) administering a bioactive agent tethered to a first capture ligand to a cell comprising a cellular target of the bioactive agent under conditions such that the cellular target binds the bioactive agent; (b) contacting the first capture ligand with a solid surface displaying a second capture ligand bound to a fusion of a first capture protein and a second capture protein, wherein the second capture protein and the second capture ligand are covalently bound; and (c) separating the solid surface from the cell lysate. In some embodiments, methods comprise a step of lysing the cell to form a lysate. In some embodiments, the cellular target is a fusion with a reporter. In some embodiments, the product of steps (a) and/or (b) exits the cells (e.g., secreted, exocytosis, active removal) without cell lysis.

In some embodiments, the present invention provides cell lysate, cell component, or cell fraction, of a cell comprising: (a) a cellular target of a bioactive agent, and (b) a bioactive agent tethered to a first capture ligand; the cell lysate further comprising: (c) a fusion of a first capture protein and a second capture protein, wherein the first capture ligand forms a covalent bond with the first capture protein upon interaction thereof, and (d) a solid surface displaying a second capture ligand, wherein the second capture ligand forms a covalent bond with the second capture protein upon interaction thereof. In some embodiments, (a) comprises a plurality of cellular targets of a bioactive compound. In some embodiments, the cellular target is a fusion with a reporter. In some embodiments, the reporter is a bioluminescent reporter. In some embodiments, the reporter is a portion, component, or subunit of a bioluminescent protein. In some embodiments, the bioluminescent reporter comprises a polypeptide with at least 70% sequence identity with SEQ ID NO.: 3 (e.g., 75%, 80%, 85%, 90%, 95%, 98%, 99%). In some embodiments, the first and second capture proteins both comprise at least 70% sequence identity with SEQ ID NO.: 1 (e.g., 75%, 80%, 85%, 90%, 95%, 98%, 99%). In some embodiments, the fusion is a homodimer. In some embodiments, the bioactive agent is a small molecule. In some embodiments, the cellular target is a binding partner of the bioactive agent. In some embodiments, the cellular target comprises a combination of molecules, such as a complex of two or more proteins, or proteins and nucleic acids. In some embodiments, the first capture ligand and second capture ligand comprise the same molecular structure. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, the cellular target is bound to the bioactive agent, the first capture protein is bound to the first capture ligand, and the second capture protein is bound to the second capture ligand on the solid surface.

In some embodiments, the present invention provides compositions and systems (e.g., cells, reaction mixture, kit, container, etc.) comprising one or more (e.g., all) of: (a) a cellular target of a bioactive agent; (b) the bioactive agent tethered to a capture ligand; and (c) a solid surface displaying a capture protein, wherein the capture protein forms a covalent bond with the capture ligand upon interaction thereof. In some embodiments, (a) comprises a plurality of cellular targets of a bioactive compound. In some embodiments, the cellular target is endogenous to a cell. In some embodiments, the cellular target is expressed intracellularly as a fusion with a reporter. In some embodiments, the reporter is a bioluminescent reporter. In some embodiments, the reporter is a portion, component, or subunit of a bioluminescent protein. In some embodiments, the bioluminescent reporter comprises a polypeptide with at least 70% sequence identity with SEQ ID NO.: 3. In some embodiments, the capture protein comprises at least 70% sequence identity with SEQ ID NO.: 1. In some embodiments, the invention comprises an additional step (e) measuring bioluminescence bound to, or released from, the solid surface. In some embodiments, the bioactive agent is a small molecule. In some embodiments, the small molecule is a synthetic molecule. In some embodiments, the small molecule is an inhibitor of protein function, such as an inhibitor of an enzyme or a receptor. In some embodiments, the cellular target comprises a combination of molecules, such as a complex of two or more proteins, or proteins and nucleic acids. In some embodiments, the cellular target is a binding partner of the bioactive agent. In some embodiments, the cellular target comprises a combination of molecules, such as a complex of two or more proteins, or proteins and nucleic acids. In some embodiments, the cellular target binds non-covalently to the bioactive agent. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, the cellular target is bound to the bioactive agent, and the capture protein is bound to the capture ligand. In some embodiments, the cellular target is bound non-covalently to the bioactive agent, and the capture protein is bound covalently to the capture ligand. In some embodiments, the capture ligand is a chloroalkane. In some embodiments, the capture ligand comprises a linker. In some embodiments, the capture ligand comprises a carbamate linker. In some embodiments, the capture ligand comprises a cleavable linker. In certain embodiments, the capture ligand comprises a carbamate linker and a cleavable linker.

In some embodiments, the present invention provides compositions and systems (e.g., reaction mixture, kit, container, etc.) comprising: (a) a bioactive agent tethered to a capture ligand; and (b) a solid surface displaying a capture protein, wherein the capture protein forms a covalent bond with the capture ligand upon interaction thereof. In some embodiments, the bioactive agent binds non-covalently to a cellular target. In some embodiments, the cellular target is endogenous to a cell. In some embodiments, the cellular target is expressed intracellularly as a fusion with a reporter. In some embodiments, the reporter is a bioluminescent reporter. In some embodiments, the bioluminescent reporter comprises a polypeptide with at least 70% sequence identity with SEQ ID NO.: 3. In some embodiments, the capture protein comprises at least 70% sequence identity with SEQ ID NO.: 1. In some embodiments, the bioactive agent is a small molecule. In some embodiments, the cellular target is a binding partner of the bioactive agent. In some embodiments, the cellular target binds non-covalently to the bioactive agent. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, the cellular target is bound to the bioactive agent, and the capture protein is bound to the capture ligand. In some embodiments, the cellular target is bound non-covalently to the bioactive agent, and the capture protein is bound covalently to the capture ligand. In some embodiments, the capture ligand is a chloroalkane. In some embodiments, the capture ligand comprises a linker. In some embodiments, the capture ligand comprises a carbamate linker. In some embodiments, the capture ligand comprises a cleavable linker. In certain embodiments, the capture ligand comprises a carbamate linker and a cleavable linker.

In some embodiments, the present invention provides methods of capturing a cellular target comprising the steps of: (a) administering a bioactive agent tethered to a capture ligand to a cell comprising a cellular target of the bioactive agent under conditions such that the cellular target binds the bioactive agent; (b) lysing the cell to produce a cell lysate; (c) contacting the cell lysate with a solid surface displaying a capture protein under conditions in which the capture protein forms a covalent bond with the capture ligand; and (d) separating the solid surface from the cell lysate. In some embodiments, the cellular target is endogenous to a cell. In some embodiments, the cellular target is expressed intracellularly as a fusion with a reporter. In some embodiments, the reporter is a bioluminescent reporter. In some embodiments, the bioluminescent reporter comprises a polypeptide with at least 70% sequence identity with SEQ ID NO.: 3. In some embodiments, the capture protein comprises at least 70% sequence identity with SEQ ID NO.: 1. In some embodiments, the bioactive agent is a small molecule. In some embodiments, the cellular target is a binding partner of the bioactive agent. In some embodiments, the cellular target binds non-covalently to the bioactive agent. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, the cellular target is bound to the bioactive agent, and the capture protein is bound to the capture ligand. In some embodiments, the cellular target is bound non-covalently to the bioactive agent, and the capture protein is bound covalently to the capture ligand. In some embodiments, the capture ligand is a chloroalkane. In some embodiments, the capture ligand comprises a linker. In some embodiments, the capture ligand comprises a carbamate linker. In some embodiments, the capture ligand comprises a cleavable linker. In certain embodiments, the capture ligand comprises a carbamate linker and a cleavable linker.

In some embodiments, the method further comprises: (e) detecting or analyzing the cellular target. In other embodiments, the method further comprises: (e) eluting the cellular target from the solid support and (f) detecting or analyzing the cellular target. In some embodiments, the cellular target is detected or analyzed using mass spectrometry (MS).

In some embodiments, the present invention provides a cell lysate of a cell comprising: (a) a cellular target of a bioactive agent; and (b) a bioactive agent tethered to a capture ligand. In some embodiments, the cell lysate further comprising: (c) a solid surface displaying a capture protein, wherein the capture protein forms a covalent bond with the capture ligand upon interaction thereof. In some embodiments, (a) comprises a plurality of cellular targets of a bioactive compound. In some embodiments, the cellular target is endogenous to the cell. In some embodiments, the cellular target is a fusion with a reporter. In some embodiments, the reporter is a bioluminescent reporter. In some embodiments, the reporter is a portion, component, or subunit of a bioluminescent protein. In some embodiments, the bioluminescent reporter comprises a polypeptide with at least 70% sequence identity with SEQ ID NO.: 3. In some embodiments, the capture protein comprises at least 70% sequence identity with SEQ ID NO.: 1. In some embodiments, the bioactive agent is a small molecule. In some embodiments, the small molecule is a synthetic molecule. In some embodiments, the small molecule is an inhibitor of protein function, such as an inhibitor of an enzyme or a receptor. In some embodiments, the cellular target is a binding partner of the bioactive agent. In some embodiments, the cellular target comprises a combination of molecules, such as a complex of two or more proteins, or proteins and nucleic acids. In some embodiments, the cellular target binds non-covalently to the bioactive agent. In some embodiments, the solid surface is a selected from the list consisting of: well, tube, slide, plate, matrix, resin, micro fluidics channel, capillary, bead, particle (e.g., microparticle, nanoparticle, etc.), etc. In some embodiments, the cellular target is bound to the bioactive agent, and the capture protein is bound to the capture ligand. In some embodiments, the cellular target is bound non-covalently to the bioactive agent, and the capture protein is bound covalently to the capture ligand. In some embodiments, the capture ligand is a chloroalkane. In some embodiments, the capture ligand comprises a linker. In some embodiments, the capture ligand comprises a carbamate linker. In some embodiments, the capture ligand comprises a cleavable linker. In certain embodiments, the capture ligand comprises a carbamate linker and a cleavable linker.

BRIEF DESCRIPTION OF DRAWINGS

FIGS. 8A-B shows (A) a Western blot demonstrating specific pull down of DHFR (21 kDa) with Methotrexate-CA, and (B) mass spectrometry analysis of proteins pulled down by Methotrexate-CA from HEK293 cells.

FIGS. 9A-B shows (A) a Western blot demonstrating specific pull down of p38 (41 kDa) with BIRB-CA, and (B) mass spectrometry analysis of proteins pulled down by BIRB-CA from HEK293 cells.

DEFINITIONS

As used herein, the term "capture protein" refers to a protein which forms a stable covalent bond with its substrate and/or ligand upon interaction therewith. A capture protein may be a receptor that forms a covalent bond upon binding its ligand or an enzyme that forms a covalent bond with its substrate. An example of a suitable capture protein for use in embodiments of the present invention is the HALOTAG protein described in U.S. Pat. No. 7,425,436 (herein incorporated by reference in its entirety).

As used herein, the term "capture fusion" refers to a fusion of two or more copies of a capture protein. The term "capture dimer" may also be used to refer to the fusion of two capture proteins (e.g., heterodimer, homodimer, etc.). The capture proteins are stably linked (e.g., covalently), tethered, and/or fused in a manner such that each capture protein within the fusion is capable of forming a covalent bond with a substrate and/or ligand. The capture proteins may be attached directly to each other or may be separated by a linker (e.g., peptide or other chain or polymer). The capture proteins may be expressed as a fusion protein (e.g., with or without a linker) or may be chemically or enzymatically linked post-expression.

As used herein, the term "capture ligand" refers to a ligand, substrate, etc. that forms a covalent bond with a capture protein upon interaction therewith. An example of a suitable capture ligand for use in embodiments of the present invention is the HALOTAG ligand described in U.S. Pat. No. 7,425,436 (herein incorporated by reference in its entirety).

As used herein, the term "cellular target" refers to a protein, polypeptide, nucleic acid (e.g., DNA or RNA), polysaccharide or a complex comprising any of these with a polypeptide(s). A cellular target could be composed of more than one component, subunit or polypeptide, e.g., the cellular target is a protein complex. Examples of a cellular target may include a receptor or an enzyme.

As used herein, the term "bioactive agent" refers generally to any physiologically or pharmacologically active substance or a substance suitable for detection. In some embodiments, a bioactive agent is a potential therapeutic compound (e.g., small molecule, peptide, nucleic acid, etc.), or drug-like molecule. Bioactive agents for use in embodiments described herein are not limited by size or structure.

DETAILED DESCRIPTION

The present invention provides compositions and methods for capture and identification of the cellular targets of a bioactive agent. In particular, provided herein are bioactive agents tethered to capture ligand, cellular targets (endogenous or optionally tagged with a reporter), capture proteins (optionally present as capture fusions), surfaces (e.g., displaying capture ligands, capture proteins or capture fusions) and methods of capturing and identifying the cellular targets of a bioactive agent therewith.

Figure 1:
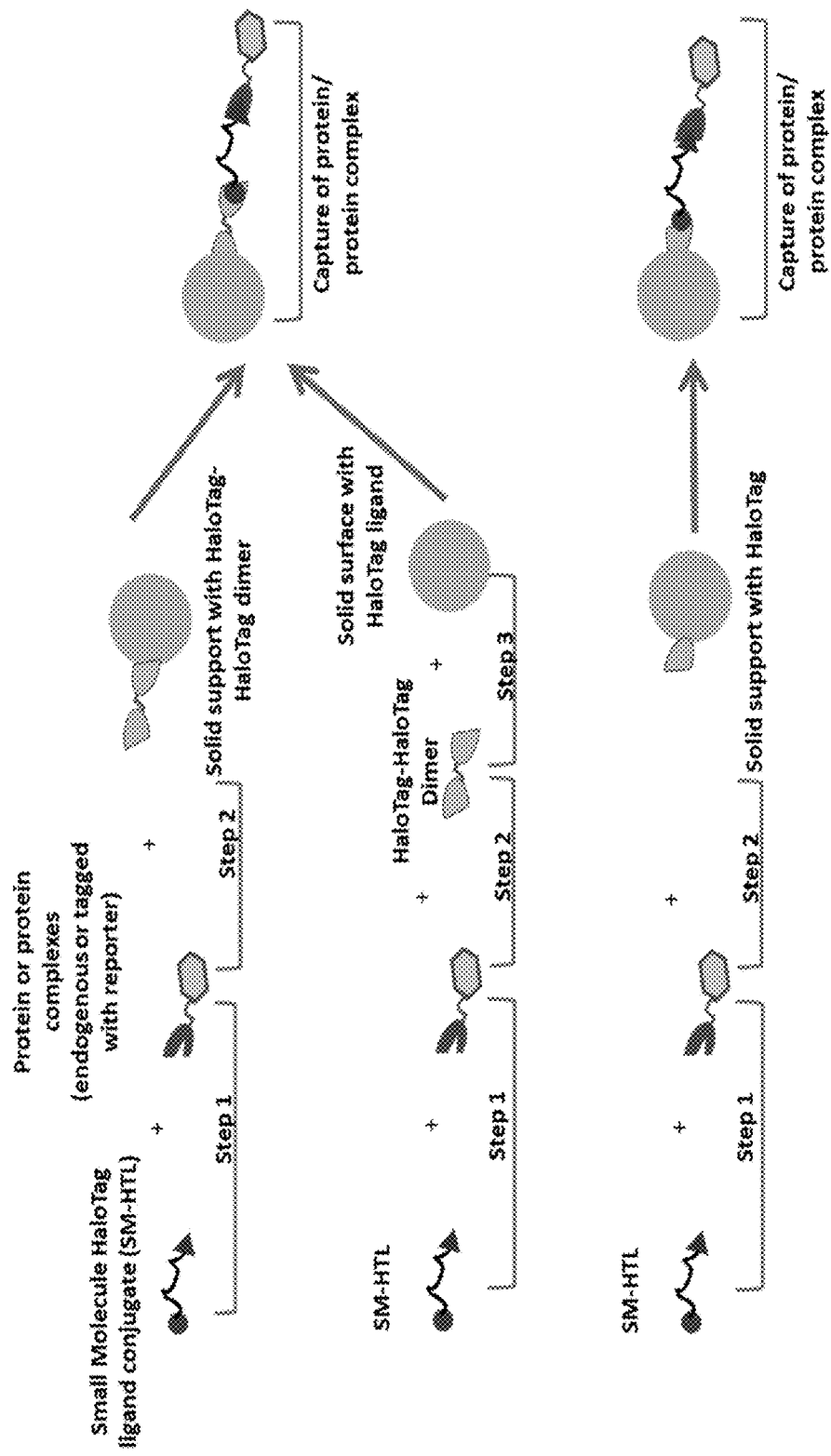
FIG. 1 shows a schematic representation of embodiments of the present invention for rapid and specific capture of bioactive agent tethered to a capture ligand (e.g., SM-HTL) complexed with protein or protein complexes using a capture protein (e.g. HALOTAG).

In certain embodiments, the present invention provides a sensitive method for discovery and validation of the cellular targets (e.g., protein or protein complex(es)) of bioactive agents (e.g., small and/or drug-like molecules) in cells (See FIG. 1). In some embodiments, the present invention finds use as a part of, or a companion to, phenotypic screening assays. For example, a set of small molecules that yield the desired phenotypic response in a phenotypic screen are each tethered to capture ligands (e.g., HALOTAG ligand) by chemical synthesis or enzymatic means. Cells are treated with the small molecule/capture ligand conjugate (e.g., small molecule-HALOTAG ligand conjugate (SM-HTL)) which engages the cellular target (endogenous or optionally fused with a reporter) and re-generates the phenotypic response (e.g., same response, similar response (e.g., ±1% ... ±2% ... ±5% ... ±10% ... ±20% ... ±30% ... ±50%, etc.). In some embodiments, cells are then lysed, and the cellular target, now linked to the capture ligand through bioactive agent, is captured by binding of the capture ligand (e.g., HALOTAG ligand) with a capture fusion (e.g., HALOTAG dehalogenase (e.g., dehalogenase modified to covalently bind its substrate)) or capture protein (e.g., HALOTAG dehalogenase (e.g., dehalogenase modified to covalently bind its substrate)) displayed surface. In some embodiments, the capture fusion is in solution (and is subsequently bound to a solid surface). In other embodiments, the capture protein or capture fusion is bound to a solid surface (e.g., well, tube, slide, plate, matrix, resin, micro fluidics channel, capillary, bead, particle (e.g., microparticle, nanoparticle, etc.), etc. (e.g., capture fusion is bound to surface displaying capture ligands on its surface)). In some embodiments, once the cells are lysed, the cellular target, now linked to the capture ligand through bioactive agent, is captured by binding of the capture ligand (e.g., HALOTAG ligand) with a capture protein (e.g., not a dimer) displayed on a solid surface (e.g., well, tube, slide, plate, matrix, resin, micro fluidics channel, capillary, bead, particle (e.g., microparticle, nanoparticle, etc.), etc.) (See FIG. 1, bottom scheme).

In some embodiments, methods are provided for the capture or "pull down" of endogenous targets (e.g., known and unknown targets of a small molecule). In some embodiments, endogenous proteins bound to a small molecule/capture ligand conjugate (e.g., (SM-HTL) are then covalently bound (e.g., pulled down) by a capture protein (e.g., displayed on a surface (e.g., well, tube, slide, plate, matrix, resin, micro fluidics channel, capillary, bead, particle (e.g., microparticle, nanoparticle, etc.), etc.)). Such pull-down methods can be followed by analysis to identify the proteins captured (e.g., following elution of the endogeneous target from the surface). Analysis techniques may include Western blotting, gel electrophoresis, mass spectrometry, nuclear magnetic resonance spectroscopy, etc. The systems, compositions, and methods provided herein provide numerous advantages when used in such a context. In certain embodiments, binding of a chloroalkane-drug conjugate (e.g., HTL-SM) in cells promotes specific interactions leading to higher probability of capturing low affinity targets. In some embodiments, the speed and efficiency of the methods provided herein (e.g., <30 minutes for covalent capture of endogenous targets (e.g., <25 minute, <20 minutes, <15 minutes, <10 minutes, <5 minutes, <1 minute) minimizes complex collapses (e.g., preserves identification of secondary targets (e.g., proteins non-covalently interacting with targets bound by a SM-HTL) and preserves low affinity interactions. In other embodiments, rapid capture minimizes non-specific capture. In certain embodiments, release of endogenous targets by competition with unconjugated drug reduces background which increases detection of low abundance targets.

Figure 2:
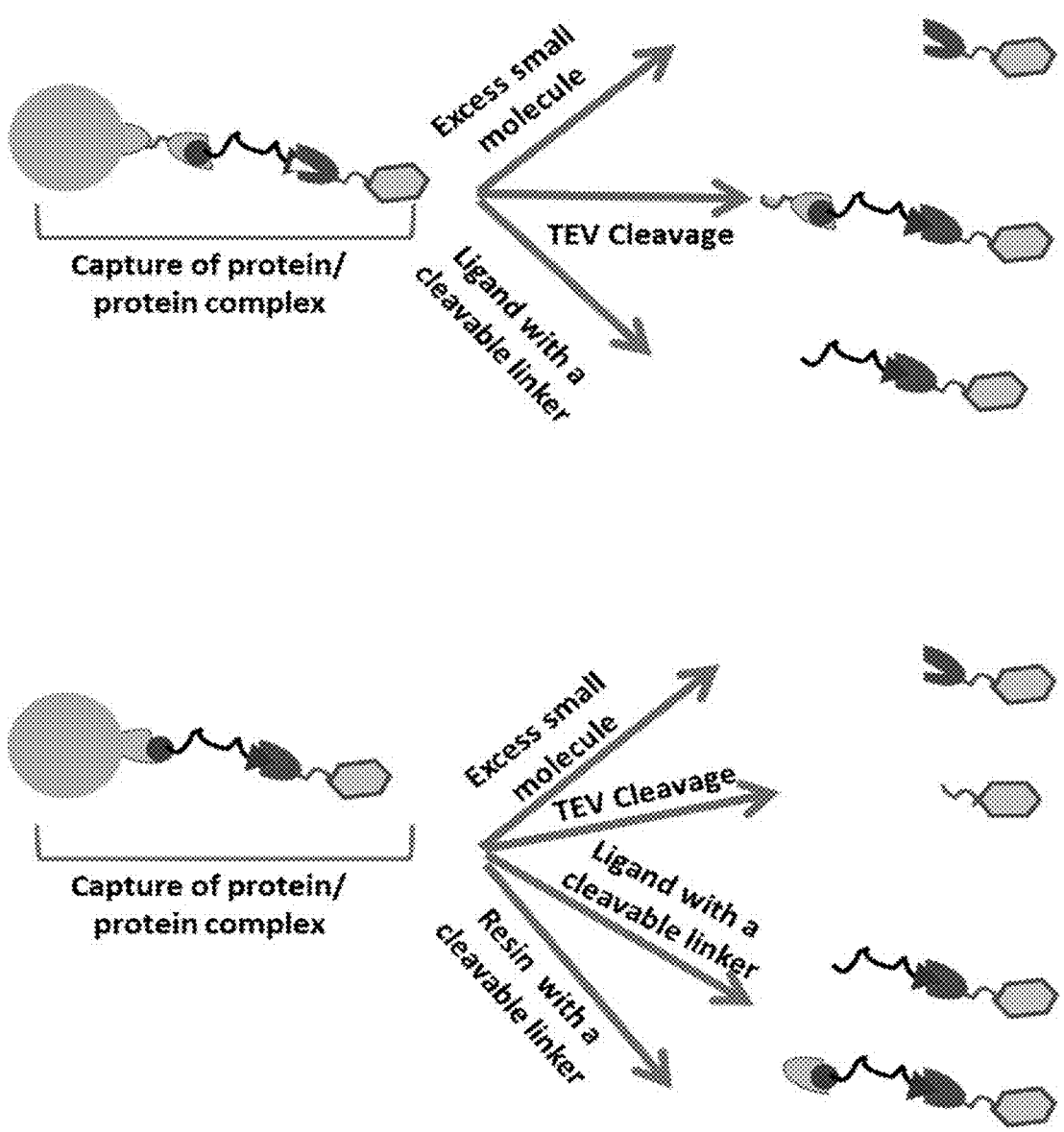
FIG. 2 shows a schematic representation of embodiments of the present invention for rapid and specific elution of protein complexes using various methods.
Figure 3A:
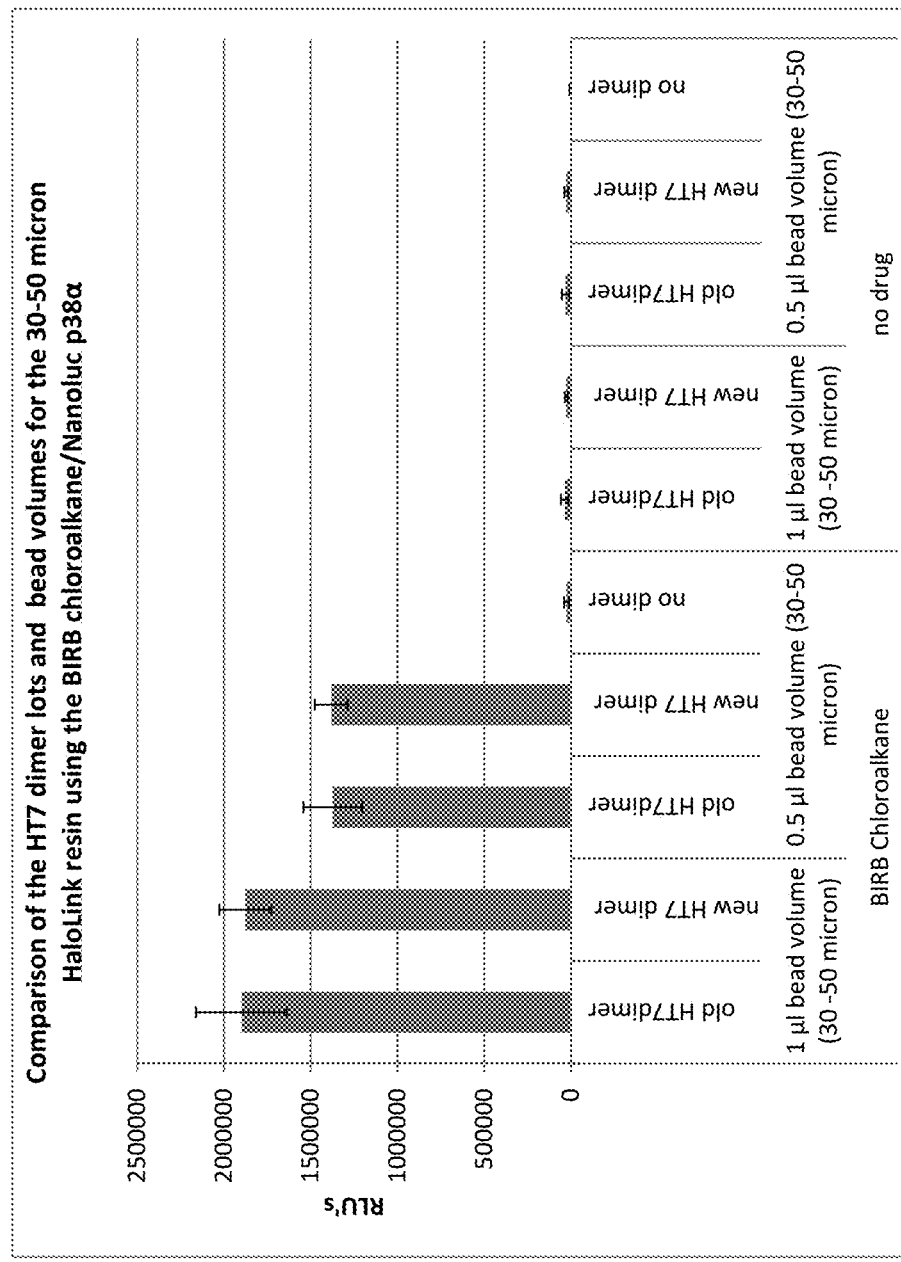
FIGS. 3A-C shows graph depicting the effect of bead volume, and the presence or absence of SM-HTL on luminescence in various capture assays: (A) p38α and BIRB-chloroalkane, (B) HDAC6 and SAHA-chloroalkane; (C) BIRB-chloroalkane pull-down with overexpressed NANOLUC-p38α; and (D) SAHA-chloroalkane pull-down with overexpressed NANOLUC-HDAC6
Figure 3B:
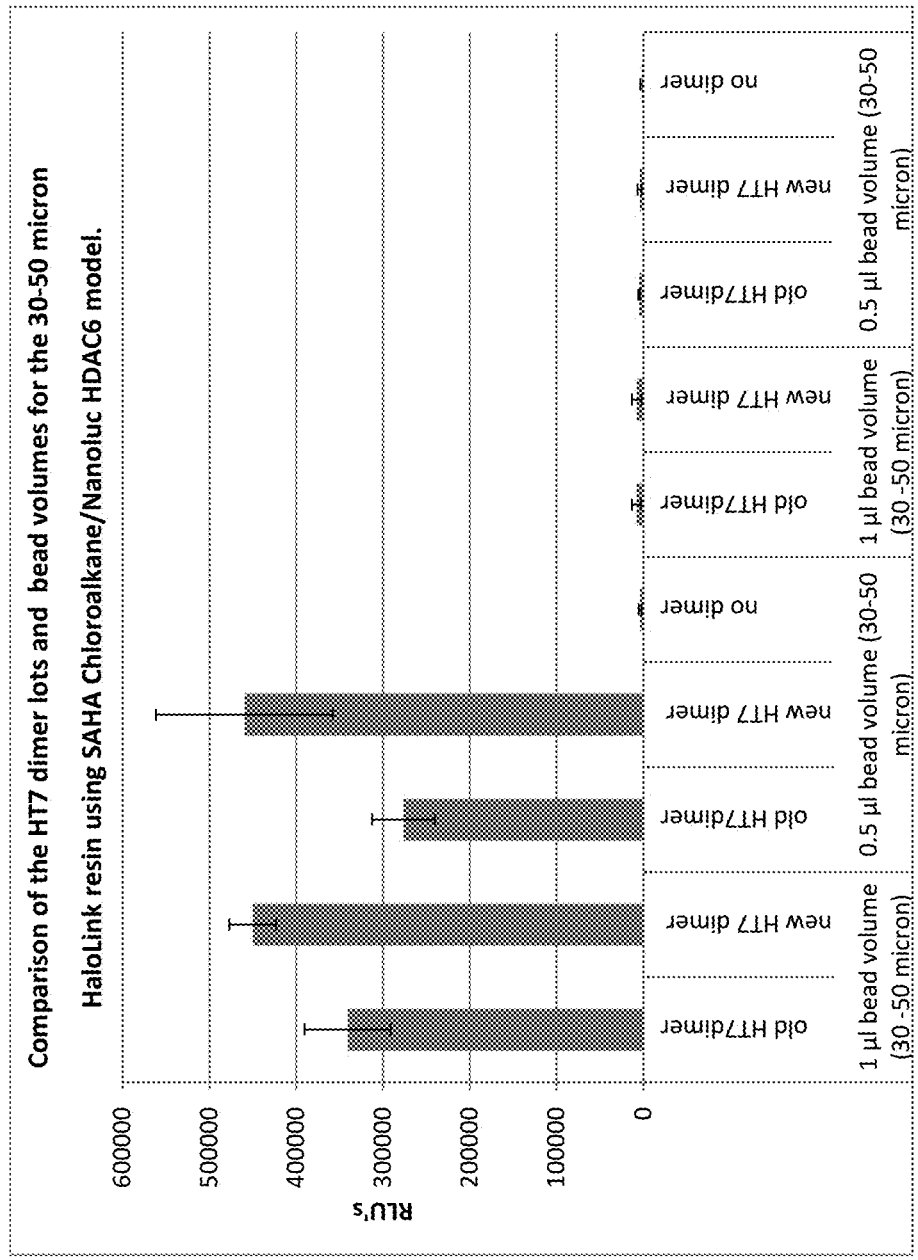
Figure 3C:
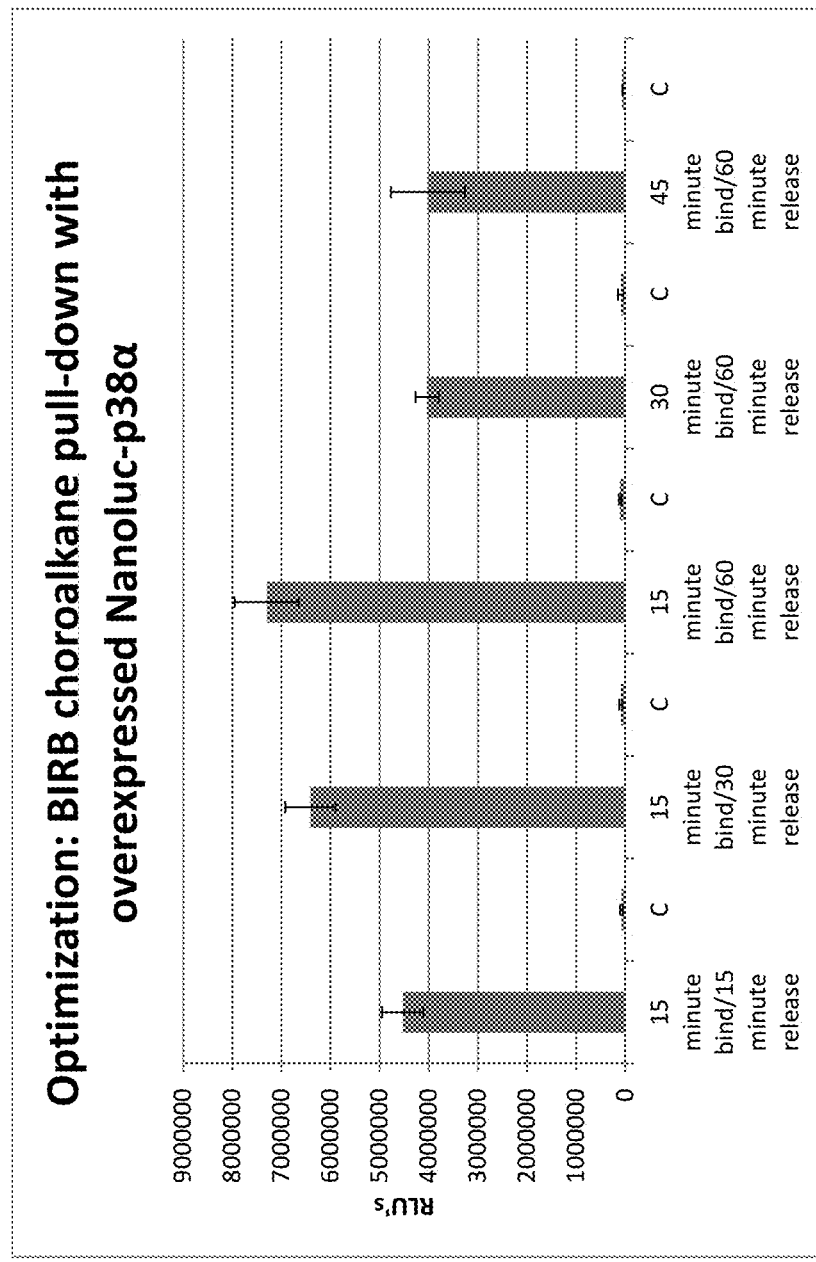
Figure 3D:
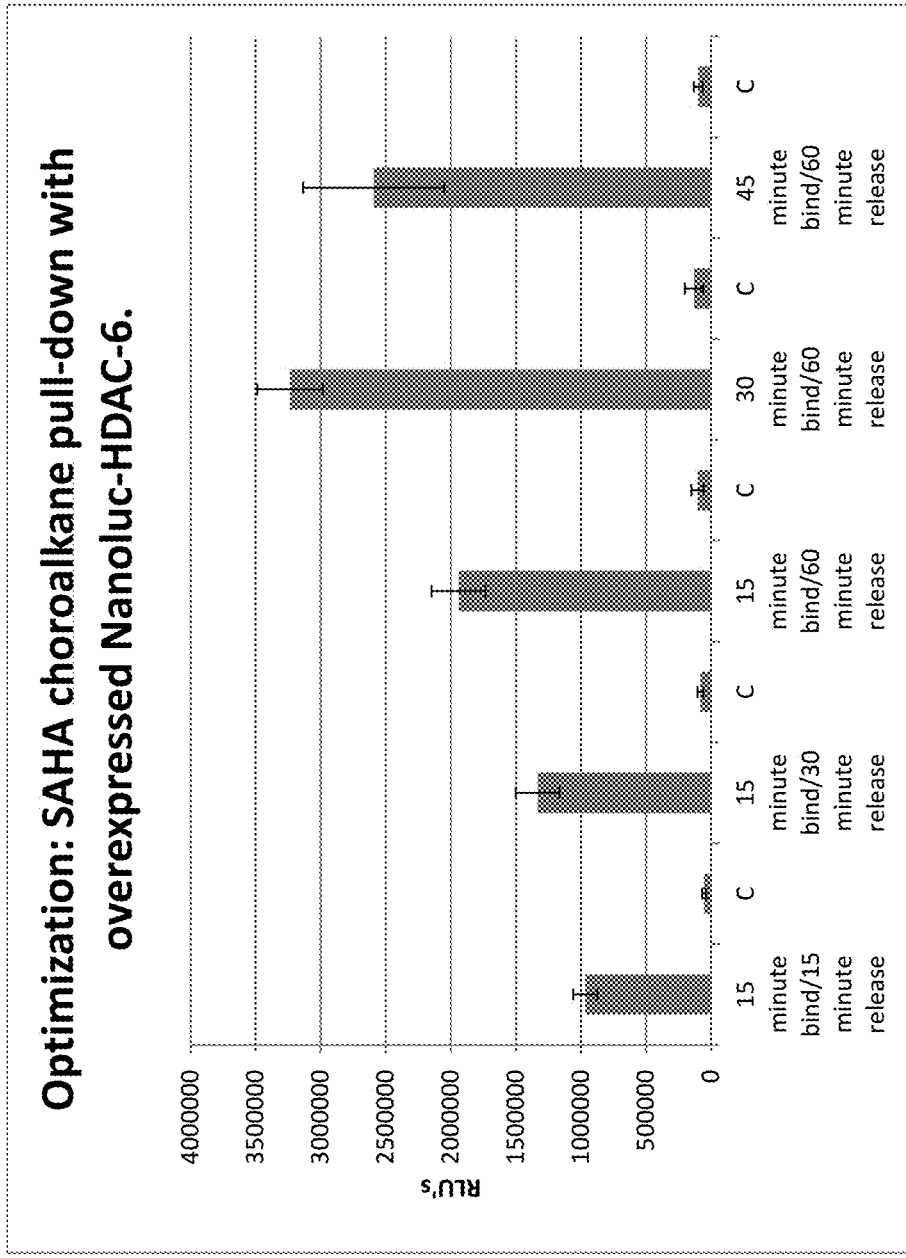

In certain embodiments, after purification of the surface-(capture ligand)-(capture fusion)-(capture ligand)-(bioactive agent)-(cellular target) complex (e.g., by purifying the surface (e.g., mechanical separation, washing, etc.), the cellular target is released or eluted from the solid surface (e.g., well, tube, slide, plate, matrix, resin, micro fluidics channel, capillary, bead, particle (e.g., microparticle, nanoparticle, etc.), etc.) by any suitable mechanism (See FIG. 2, top scheme). In some embodiments, excess untethered bioactive agent is added to the system to compete the cellular target away from the capture-ligand-tethered bioactive agent. In other embodiments, the linkage (e.g., TEV protease cleavage site) between the two capture proteins of the capture fusion is cleaved (e.g., chemically, enzymatically) to release the (capture protein)-(capture ligand)-(bioactive agent)-(cellular target) complex. In still other embodiments, the linkage between the capture ligand and bioactive agent is cleaved (e.g., chemically, enzymatically) to release the (bioactive agent)-(cellular target) complex. In some embodiments, all or a portion of a linker remains attached to one or both released components following cleavage.

In other embodiments, after purification of the surface-(capture protein)-(capture ligand)-(bioactive agent)-(cellular target) complex (e.g., by purifying the surface (e.g., mechanical separation, washing, etc.), the cellular target is released or eluted from the solid surface (e.g., well, tube, slide, plate, matrix, resin, micro fluidics channel, capillary, bead, particle (e.g., microparticle, nanoparticle, etc.), etc.) by any suitable mechanism (See FIG. 2, bottom scheme). In some embodiments, excess untethered bioactive agent is added to the system to compete the cellular target away from the capture-ligand-tethered bioactive agent. In other embodiments, the linkage (e.g., TEV protease cleavage site) between the reporter and cellular target is cleaved (e.g., chemically, enzymatically) to release the reporter. In other embodiments, the linkage between the capture ligand and bioactive agent is cleaved (e.g., chemically, enzymatically) to release the (bioactive agent)-(cellular target) complex. In still other embodiments, the capture protein is released from the surface, thereby releasing the entire (capture protein)-(capture ligand)-(bioactive agent)-(cellular target) complex.

In any embodiments, in which the cellular target is fused/linked to a reporter, the reporter remains linked to any complex comprising the cellular target, unless otherwise specified (e.g., upon cleaving of the link between the cellular target and reporter).

In some embodiments in which the cellular target is attached/fused to a reporter molecule (e.g., fluorophore, luciferase, etc.), the cellular target, liberated from the capture complex, is detected by generating and/or detecting a signal from the reporter. In other embodiments in which the cellular target is attached/fused to a reporter molecule (e.g., fluorophore, luciferase, etc.), the cellular target, still bound to the capture complex, is detected by generating and/or detecting a signal from the reporter. In some embodiments (e.g., in which the cellular target is not attached/fused to a reporter molecule), the cellular target, liberated from the capture complex, is characterized and/or identified (e.g., by biophysical and/or biochemical analysis (e.g., mass spectrometry, spectroscopy, etc.).

Capture of cellular targets of bioactive agents is facilitated by the interaction (e.g., covalent or non-covalent) of a capture ligand (e.g., small molecule (e.g., HALOTAG ligand)) with a capture protein (e.g., receptor protein, HALOTAG dehalogenase, etc.). In certain embodiments, the capture ligand/capture protein interaction occurs twice, in separate steps of the capture systems and methods described herein (See FIG. 1). First, a capture ligand is tethered, or otherwise attached, to the bioactive agent of interest. Once the bioactive agent has become bound to its cellular target (e.g., in vivo), a capture fusion (e.g., a homodimer of capture entities) is added, and the capture ligand is bound by one of the capture entities. Next, a solid support displaying a plurality of the same capture ligands is added, and the unbound half of the capture fusion binds to the surface. The cellular target is now tethered to the solid support by two capture ligand/capture protein interactions (See FIG. 1). In an alternative embodiment, the capture fusion is bound to the solid support (e.g., via its interaction with surface displayed capture ligands) prior to addition to the assay (and prior to binding the capture ligand tethered to the bioactive agent. Either alternative results in the same captured configuration.

In other embodiments, a capture protein is present as a capture monomer, not a capture fusion. In some embodiments, a solid support (e.g., well, tube, slide, plate, matrix, resin, micro fluidics channel, capillary, bead, particle (e.g., microparticle, nanoparticle, etc.), etc.) is provided displaying capture monomers (e.g., HALOTAG dehalogenase) on its surface. Capture ligands tethered to bioactive agents are immobilized on the surface when the capture ligand (e.g., HALOTAG ligand) and capture protein (e.g., HALOTAG) interact. If the bioactive agent has interacted (e.g., stably, at equilibrium, etc.) with a cellular target (e.g., tagged by a reporter), the cellular target becomes linked (e.g., through the bioactive agent, capture ligand, and capture protein) to the solid support.

In certain embodiments, compositions, methods, and systems herein provide bioactive agents. In some embodiments, a conjugate of a bioactive agent and a capture ligand is provided. In some embodiments, a bioactive agent is any small molecule, macromolecule, or molecular complex capable of interacting with the biology of a cell. In some embodiments, a bioactive agent and capture ligand (e.g., HALOTAG ligand) are fused, tethered, connected, etc. by any suitable structure or mechanism (e.g., chemically linked (e.g., directly or indirectly), enzymatically linked, linked by a linker (e.g., peptide, nucleic acid, polymer, ester linkage, PEG linker, carbon chain, etc.)). The type of linkage should not be viewed as limiting.

In some embodiments, a capture ligand comprises, and/or is tethered to a bioactive agent by, a linker moiety. In some embodiments, a linker moiety is part of the capture ligand. In some embodiments, a linker moiety is added to a capture ligand via coupling chemistry for attachment to the bioactive agent. In some embodiments, a linker moiety is added to a bioactive agent via coupling chemistry for attachment to the capture ligand. The present invention is not limited to any particular linker moiety. Indeed, a variety of linker moieties are contemplated and suitable linkers could comprise, but are not limited to, alkyl. groups, methylene carbon chains, ether, poly ether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosamine oligoglycans, dendritic polymers (WO93/06868 and by Tomaiia et al. in Angew. Chem. Int. Ed. Engl. 29: 138-175 (1990), herein incorporated by reference in their entireties), PEG-chelant polymers (W94/08629, WO94/09056 and WO96/26754, herein incorporated by reference in their entireties), oligonucleotide linker, phospholipid derivatives, alkenyl chains, alkynyl chains, disulfide, or a combination thereof. In some embodiments, a linker comprises any combination of alkyl, alkenyl, alkynyl, phenyl, cycloalkyl, heterocycloalkyl, benzyl, halo, fluoro, chloro, bromo, bromo, iodo, hydroxyl, carbonyl, aldehyde, haloformyl, carbonate ester, carboxylate, carboxyl, ester, hydroperoxy, peroxy, ether, hemiacetal, hemiketal, acetal, ketal, orthoester, amide, amine, imine, imide, azide, azo, cyanate, nitrate, nitrite, nitrile, nitro, nitroso, pyridine, thiol, sulfide, disulfide, sulfoxide, sulfone, sulifinic acid, sulfonic acid, thiocyanate, thione, thial, phosphine, phosphonic acid, phosphate, and/or phosphodiester groups. Any suitable linkers, utilizing any suitable functional groups, are within the scope of embodiments of the invention. In particular embodiments, a linker is a carbamate linker. In some embodiments, a bioactive agent is attached to a capture ligand by a linker, and attachment of the entity of interest is reversible (e.g., cleavable (e.g., photocleavable, chemically cleavable, enzymatically cleavable)). In some embodiments, a linker is cell permeable. In some embodiments, the above linkers find use in attaching or tethering other components (e.g., capture proteins) described herein.

In some embodiments, a capture ligand (and linker) comprises or consists of —O(CO)NH(CH$_2$CH$_2$O)$_y$—(CH2)$_x$-halogen, wherein y is 1-8, x is 2-20, and halogen is Cl, Br, or F (e.g., —O(CO)NH(CH$_2$CH$_2$O)$_2$(CH$_2$)$_x$Cl, O(CO)NH(CH$_2$CH$_2$O)$_2$(CH$_2$)$_6$-halogen, O(CO)NH(CH$_2$CH$_2$O)$_2$(CH$_2$)$_6$—Cl, etc.).

In certain embodiments, libraries of bioactive agents (e.g., >10 agents, >50 agents, >100 agents, >500 agents, >1000 agents, >5000 agents, >10,000 agents, >50,000 agents, etc.) are provided. In some embodiments, systems, methods, and compositions are provided for screening libraries of bioactive agents for a phenotypic effect and/or activity. In some embodiments, the present invention provides means of capturing the cellular target of any bioactive agents in a library responsible for producing, eliciting, inducing, etc. phenotypic effect and/or activity. In some embodiments, the present invention provides means of capturing, identifying, characterizing, etc. the cellular target of a bioactive agent (e.g., a bioactive agent responsible for the phenotypic effect and/or activity).

In some embodiments, a cellular target comprises any suitable binding/interaction partner (e.g., receptor, enzyme) for a bioactive agent (e.g., small molecule, protein, nucleic acid, lipid, etc.). In particular embodiments, a cellular target is a protein that binds to or otherwise interacts with (e.g., stably, specifically, non-covalently, at equilibrium, etc.) a bioactive agent. In more particular embodiments, a cellular target is a receptor protein or an enzyme that binds to or otherwise interacts with (e.g., stably, specifically, non-covalently, at equilibrium, etc.) a small molecule bioactive agent. The present invention is not limited by the identity, type, or class of cellular targets. In certain embodiments, libraries of hundreds, thousands, tens of thousands, more different cellular targets find use in the present invention.

In some embodiments, the cellular target is expressed in cells in which an assay is to be performed. In some embodiments, the cellular target is expressed at or near the endogenous levels (e.g., native abundance) for the cellular target (e.g., no overexpression of cellular targets). In some embodiments, methods herein allow for capture of cellular targets present in cells at or near their natural or endogenous abundance, thereby maximizing the biological relevance of an assay. In certain embodiments, because the methods allow for capture at endogenous levels of cellular target, the methods are useful for the capture of unknown targets of a bioactive agent (e.g., those that one would not see fit to overexpress). In some embodiments, the cellular target is endogenous to the cell.

In a specific exemplary embodiment, the capture protein is a dehalogenase enzyme modified to form covalent bonds with its substrate (See, e.g., U.S. Pat. Nos. 7,425,436; 7,429,472; 7,867,726; 7,888,086; 7,935,803; RE42,931; 8,168,405; 8,202,700; 8,257,939; herein incorporated by reference in their entireties), referred to herein as a "HALOTAG dehalogenase," and the capture ligand is a substrate for a HALOTAG dehalogenase, for example, a haloalkane, reference to herein as a "HALOTAG ligand." In some embodiments, a capture protein comprises a polypeptide with at least 70% sequence identity (e.g., 75% identity, 80% identity, 85% identity, 90% identity, 95% identity, 98% identity, 99% identity) with SEQ ID NO.: 1. In some embodiments, the capture ligand comprises a carbamate linker. In certain embodiments, the capture ligand is a chloroalkane ligand with a carbamate linker, e.g., a carbamate chloroalkane.

In some embodiments, a reporter is an entity capable of generating, exhibiting, and/or emitting a signal (e.g., fluorescence, resonance energy, etc.) when triggered by specific conditions (e.g., upon energy absorption). In certain embodiments, compositions, methods, and systems herein provide a fusion of a cellular target and a reporter (e.g., bioluminescent reporter (e.g., luciferase (e.g., NANOLUC))). In some embodiments, a cellular target and reporter are fused, tethered, connected, etc. by any suitable structure or mechanism (e.g., expressed as a fusion construct (e.g., with or without peptide linker), chemically linked (e.g., directly or indirectly), enzymatically linked, linked by a linker (e.g., peptide, nucleic acid, other polymer (e.g., ester linkage, PEG linker, carbon chain, etc.)).

In some embodiments, the reporter is a bioluminescent reporter (e.g., expressed as a fusion protein with the cellular target). In certain embodiments, the bioluminescent reporter is a luciferase. In some embodiments, a luciferase is selected from those found in *Omphalotus olearius*, fireflies (e.g., Photinini), *Renilla reniformis*, Aequoria, mutants thereof, portions thereof, variants thereof, and any other luciferase enzymes suitable for the systems and methods described herein. In some embodiments, the bioluminescent reporter is a modified, enhanced luciferase enzyme from *Oplophorus* (e.g., NANOLUC enzyme from Promega Corporation, SEQ ID NO: 3 or a sequence with at least 70% identity (e.g., >70%, >80%, >90%, >95%) thereto). In some embodiments, the protein sensor is a thermostable *Photuris pennsylvanica* luciferase. Exemplary bioluminescent reporters are described, for example, in U.S. Pat. App. No. 2010/0281552 and U.S. Pat. App. No. 2012/0174242, both of which are herein incorporated by reference in their entireties.

In some embodiments, the bioluminescent reporter comprises NANOLUC (See U.S. Pat. App. Nos. 2010/0281552 and 2012/0174242, herein incorporated by reference in their entireties). In some embodiments, the bioluminescent reporter comprises a polypeptide with at least 70% identity (e.g., >70%, >80%, >90%, >95%) to SEQ ID NO: 3 that retains bioluminescent characteristics. In certain embodiments, the use of the NANOLUC enzyme, or a variant thereof, provides features (e.g., signal intensity, brightness, high light output, narrow spectrum, etc.) that enable detection of capture cellular target (e.g., at low concentration). In some embodiments, the high light output of NANOLUC enables the low concentration (e.g., <1 μM, <100 nM, <10 nM, <1 nm, etc.) of assay components (e.g., DNA for expression of NANOLUC) useful to carry out assays under physiologically relevant conditions. In some embodiments, NANOLUC enables detection of captured cellular targets identified in a phenotypic screen.

In some embodiments, a substrate for the bioluminescent reporter is provided. In some embodiments, the bioluminescent reporter converts the substrate into a reaction product and releases light energy, e.g., luminescence, as a byproduct. In some embodiments, the substrate is a substrate for a luciferase enzyme. In some embodiments, the substrate is a substrate for a modified, enhanced luciferase enzyme from *Oplophorus*, e.g., NANOLUC enzyme from Promega Corporation (e.g., SEQ ID NO: 3). In some embodiments, the substrate comprises coelenterazine, a coelenterazine derivative, a structural or functional equivalent of coelenterazine, a molecule substantially equivalent to coelenterazine (e.g., structurally and/or functionally), or molecule functionally or structurally similar to coelenterazine. In some embodiments, the bioluminescent reporter converts the coelenterazine, coelenterazine derivative, structural or functional equivalent of coelenterazine, or substantial equivalent to coelenterazine into coelenteramide, a coelenteramide derivative, a structural or functional equivalent of coelenteramide, or a substantial equivalent to coelenteramide and releases light energy as a byproduct.

In some embodiments, a cellular target is detected based on a characteristic of an attached reporter (e.g., fluorescence, luminescence, mass (e.g., by mass spectrometry (MS)), radioactivity, enzymatic activity, etc.). In some embodiments, a cellular target is detected based on a characteristic of the cellular target (e.g., fluorescence, luminescence, mass (e.g., by mass spectrometry (MS)), radioactivity, etc.).

In certain embodiments, the present invention provides a fusion of multiple (e.g. two) capture proteins. In some embodiments, both capture proteins retain their activity when fused (e.g., dimerized). In some embodiments, both capture proteins retain the ability to covalently bind their respective capture ligand. In some embodiments, a capture fusion is a heterodimer of two different capture proteins (e.g., that bind different capture ligands). In other embodiments, a capture fusion is a homodimer of two capture proteins with the same amino acid sequence that bind the same capture ligands. In some embodiments, two capture proteins are covalently linked. In some embodiments, the capture proteins are linked end-to-end (e.g., N—C—N—C, N—C—C—N, C—N—N—C, C—N—C—N). In some embodiments, a capture fusion is expressed as two fused proteins. In some embodiments, two capture proteins are attached post-expression (e.g., chemically, enzymatically, etc.) to produce a capture fusion. In some embodiments, the capture proteins (e.g., HALOTAG proteins) are fused, tethered, connected, etc. by any suitable structure or mechanism (e.g., expressed as a fusion, chemically linked (e.g., directly or indirectly), enzymatically linked, linked by a linker (e.g., peptide, nucleic acid, polymer, ester linkage, PEG linker, carbon chain, etc.)). The type of linkage should not be viewed as limiting. In some embodiments, the two capture proteins are directly linked. In some embodiments, the two capture proteins are separated by a linker. Any suitable linker (e.g., peptide (e.g., with protease cleavage site (e.g., TEV cleavage site)), other polymer, alkyl chain, substituted alkyl chain, etc.) may find use in connecting the capture proteins of a capture fusion. In some embodiments, one or both of the capture proteins comprise 70% or greater (e.g., 75%, 80%, 85%, 90%, 95%, 98%, 99%) sequence identity to SEQ ID NO: 1.

In some embodiments, the present invention provides a capture protein as a monomer (e.g., not as a capture fusion). In some embodiments, a capture protein is linked to a solid surface (e.g., well, tube, slide, plate, matrix, resin, micro fluidics channel, capillary, bead, particle (e.g., microparticle, nanoparticle, etc.), etc.). In some embodiments, a plurality of capture proteins (e.g., as monomers) are attached to a surface. In some embodiments, a capture protein (e.g., HALOTAG proteins) is fused, tethered, connected, etc. by any suitable structure or mechanism (e.g., expressed as a fusion, chemically linked (e.g., directly or indirectly), enzymatically linked, linked by a linker (e.g., peptide, nucleic acid, polymer, ester linkage, PEG linker, carbon chain, etc.)). The type of linkage should not be viewed as limiting.

In certain embodiments, the present invention provides a sensitive method for discovery and validation that proteins or protein complexes are the binding target of bioactive small molecules in cells. In some embodiments, methods involve selecting a library of small molecules with the desired phenotypic response (e.g., as determined from a phenotypic screen) and attaching a capture ligand (e.g., HALOTAG ligand) by any suitable means (e.g., chemical synthesis). Cells are then treated with the small molecule/capture ligand (SM/CL) to re-generate the phenotypic response. In some embodiments, SM/CL compounds are cell permeable. In some embodiments, cell permeability enables regeneration of the phenotypic response. In some embodiments, chloroalkanes and carbamates are well-suited to preserving and/or enhancing cell permeability. In some embodiments, cells are then lysed, and SM/CL attached to protein or protein complexes are captured. In some embodiments, capture of SM/CL bound to protein complexes is mediated by a fusion of two capture proteins (aka "capture fusion" or "capture dimer") that allows rapid capture to minimize dissociation of protein interactors and/or reduces the non-specific binding of other proteins. In some embodiments, capture is done on solid support with low non-specific binding properties. In some embodiments, target proteins (e.g., cellular targets) are eluted with high specificity, further reducing the background hence enabling better target identification.

In some embodiments, capture fusions (e.g., HALOTAG dimer) or a capture protein (e.g., HALOTAG) in conjunction with a small molecule/HALOTAG ligand conjugate is useful for validation of positive interactions in a high-throughput format.

In some embodiments, a capture fusion (e.g., HALOTAG dimer) or capture protein (e.g., HALOTAG) is provided for rapid capture of SM-CL bound to a cellular target (e.g., protein or protein complex). In some embodiments, a HALOTAG dimer or capture protein (e.g., HALOTAG) is used for capture of a bioactive agent/HALOTAG ligand conjugate bound to a cellular target of the bioactive agent. Characteristics of the HALOTAG dimer and/or HALOTAG protein that provide advantages over other capture systems, for example a) rapid kinetics of the reaction of HALOTAG with HALOTAG ligand (e.g., even when the ligand is complexed with a large protein or protein complex) and b) rapid capture accomplished using two different formats (FIG. 1). In some embodiments, a HALOTAG dimer (or another capture fusion) or HALOTAG protein (or other capture protein) is used to make HALOTAG protein beads (or other protein capture beads) for covalent capture of HALOTAG ligand (or other capture ligand). HALOTAG (or other capture protein) is oriented for to preserve functional efficiency. Moreover, the HALOTAG dimer binding to the beads is quantitative, thereby allowing accurate control of the protein density at the bead surface. In other embodiments, HALOTAG dimer (or another capture fusion) is added to the solution in a certain stoichiometric excess to small molecule/HALOTAG ligand (or other capture ligand) to take advantage of rapid solution based kinetics for binding of small molecule/HALOTAG ligand (or other capture ligand) and protein complex. In some embodiments, a surface displaying a capture fusion, capture protein, capture ligand, and/or an optimized HALOLINK bead is used for specific capture of complex. In some embodiments, elution of protein complexes from the bead for downstream detection (e.g., mass spectrometry) is critical in identifying correct 'hit'. In some embodiments, capture fusions (e.g., HALOTAG dimer) comprises a TEV cleavage site that allows selective elution of complexes leaving behind any non-specifically bound protein (e.g., improving signal over background). In some embodiments, using a multi-well plate activated with capture ligand (e.g., HALOTAG ligand), the assay is converted to a high throughput format (e.g., for validation).

In certain embodiments, the present invention provides a surface displaying capture proteins (e.g., HALOTAG, HALOTAG dimer, etc.). In some embodiments, a surface is provided that displays ligands (e.g., HALOTAG ligand) for a capture protein on its surface. Capture fusions are added to the surface and become immobilized on the surface. The surface with capture fusions immobilized on its surface is then used to capture (capture ligand)-(bioactive agent)-(cellular target) complexes. In other embodiments, a surface is provided that displays functional groups that allow for immobilization of capture proteins to its surface. Any suitable chemistry may be used for such immobilization. Capture proteins are added to the surface and become immobilized on the surface (e.g., chemically, enzymatically, directly, through a linker, etc.). The surface with capture proteins immobilized on its surface is then used to capture (capture ligand)-(bioactive agent)-(cellular target) complexes.

EXPERIMENTAL

Example 1

Experiments were conducted during development of embodiments of the present invention to demonstrate the functionality of the capture ligand/capture fusion method of capturing a cellular target of a bioactive agent.

Figure 4:
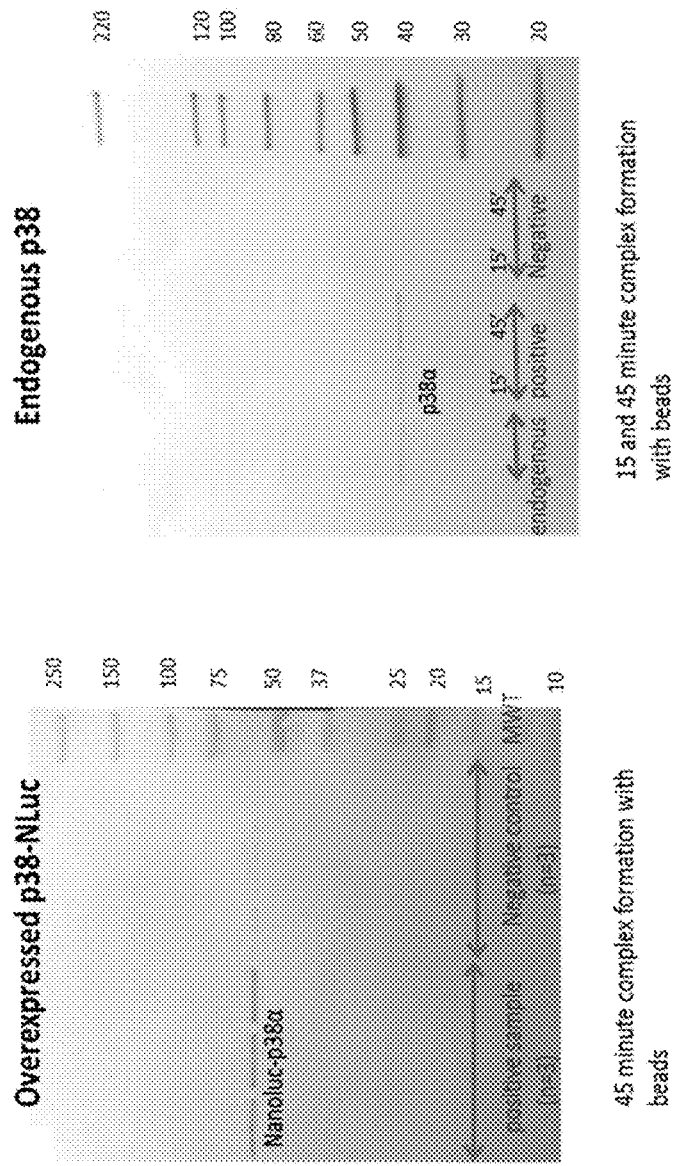
FIG. 4 shows Western/silver stain analysis using anti-p38 of lysates following a p38α and BIRB-chloroalkane capture assay.

HEK239T cells were grown in wells of 96-well or 6-well plates. The cells were transiently transfected with plasmid DNA expressing NANOLUC-p38 alpha or NANOLUC-HDAC6 (histone deacetylase 6) fusion proteins and incubated overnight at 37° C., 5% $CO_2$. 10 μM of the chloroalkane-drug conjugate BIRB-chloroalkane (for p38) or SAHA-chloroalkane (for HDAC6) was then added to the cells and incubated for 2 hours. Negative controls contained cells with no chloroalkane-drug conjugate. The media was then removed, and the cells washed in 1×PBS. The cells were lysed Mammalian Lysis Buffer (Promega Corp.) containing HALOTAG protein dimer (dimer of SEQ ID NO: 1) and DNase I for 10 minutes. MAGNE HALOLINK beads (1 μl bed volume) are then added to the lysed cells and incubated for 15 min. The lysate and beads are washed 3× at 3 minutes with shaking in wash buffer (25 mM Tris pH 7.5; 100 mM NaCl; 0.005% IGEPAL). The complex is then eluted from the beads using 150 μM unconjugated drug for an hour, and luminescence measured to detect luminescence from the NANOLUC luciferase in the elution (FIGS. 3A-D). Western/silver stain analysis of the lysates using anti-p38 was also performed (FIG. 4).

Example 2

Different amounts of a HALOTAG protein dimer (dimer of SEQ ID NO: 1) were added to cell lysates expressing a NANOLUC-p38 fusion protein (e.g., reporter/cellular-target fusion) which have or have not been treated with BIRB-chloroalkane (e.g., bioactive-agent/capture-ligand conjugate) as shown in Table 1. After 15 minute incubation, the samples were placed into wells of white, 96-well polystyrene plates activated with HALOTAG ligand (HALOLINK plates; Promega Corp.) and further incubated for 45 minutes. The wells were then washed PBS+0.05% Tween-20 (PBST). Then, 50 ul PBS followed by 50 ul of NANOGLO luciferase detection reagent was added to the wells, and luminescence measured.

Table 2 indicates differences in luminescence in samples with and without HALOTAG dimer (e.g., dimer of SEQ ID NO: 1) that indicate specific pull-down of the NANOLUC-p38 fusion protein.

TABLE 1

| 1 | 2 | 3 | 4 | 5 | 6 | 7 | 8 | 9 | 10 |
|---|---|---|---|---|---|---|---|---|---|
| | p38-Nluc expressing cells treated with drug | | | | | No drug treatment | | | |
| No HALOTAG dimer | 2 ug/well | 4 ug/well | 6 ug/well | 8 ug/well | No HALOTAG dimer | 2 ug/well | 4 ug/well | 6 ug/well | 8 ug/well |

TABLE 2

| 1 | 2 | 3 | 4 | 5 | 6 | 7 | 8 | 9 | 10 |
|---|---|---|---|---|---|---|---|---|---|
| 278085 | 236900 | 290173 | 401205 | 395510 | 223779 | 198295 | 185512 | 157721 | 178179 |
| 275690 | 397958 | 462596 | 538956 | 526903 | 286611 | 338811 | 183151 | 265931 | 324898 |
| 443682 | 431167 | 587826 | 596504 | 610628 | 378080 | 301971 | 318238 | 298925 | 232258 |

Example 3

Experiments were conducted during development of embodiments of the present invention to demonstrate the efficiency of a pull-down of a target protein from cells onto HALOTAG protein beads using chloroalkane drug conjugates. In this example, a BIRB-chloroalkane conjugate (PBI-4834, see below) was utilized to pull down a NANOLUC-p38 alpha fusion protein from living cells.

PBI4834 (BIRB Carbamate Chloroalkane)

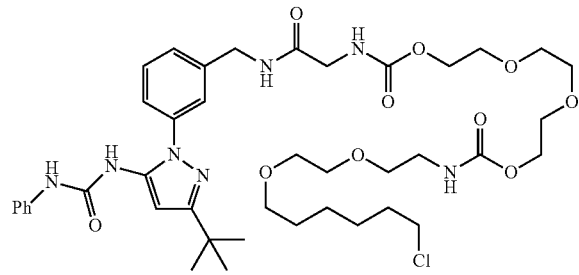 [SMILES: CC(C)(C)c1cc(NC(=O)Nc2ccccc2)n(-c2cccc(CNC(=O)CNC(=O)OCCOCCOCCOC(=O)NCCOCCOCCCCCCCl)c2)n1]

HEK293 cells in wells of a 96-well plate were transfected using PEI with plasmid DNA encoding NANOLUC-p38 fusion. Twenty-four hours post-transfection, cells were incubated with a final concentration of 10 µM PBI-4834 while control cells were not treated with the conjugated drug. Following equilibrium binding of 2 hours, the media was removed, cells were quickly washed with PBS and lysed in a detergent-based lysis buffer for 10 minutes. The cell lysates were then transferred to wells of a 96-well plate which contained 0.5 µl settled paramagnetic HALOTAG protein beads (Promega Corp.) and incubated with shaking for 15-45 minutes. Following binding, the unbound fraction was removed and the HALOTAG protein paramagnetic beads were washed. 150 uM unconjugated BIRB796 was then added and the captured NANOLUC-p38 alpha fusion was specifically released from the beads by competition with the unconjugated BIRB796 for 60 minutes. The released NANOLUC-p38 alpha fusion protein (+PBI-4834) and control (−PBI4834) was detected using NANOGLO luciferase reagent (Promega Corp.).

Figure 5:
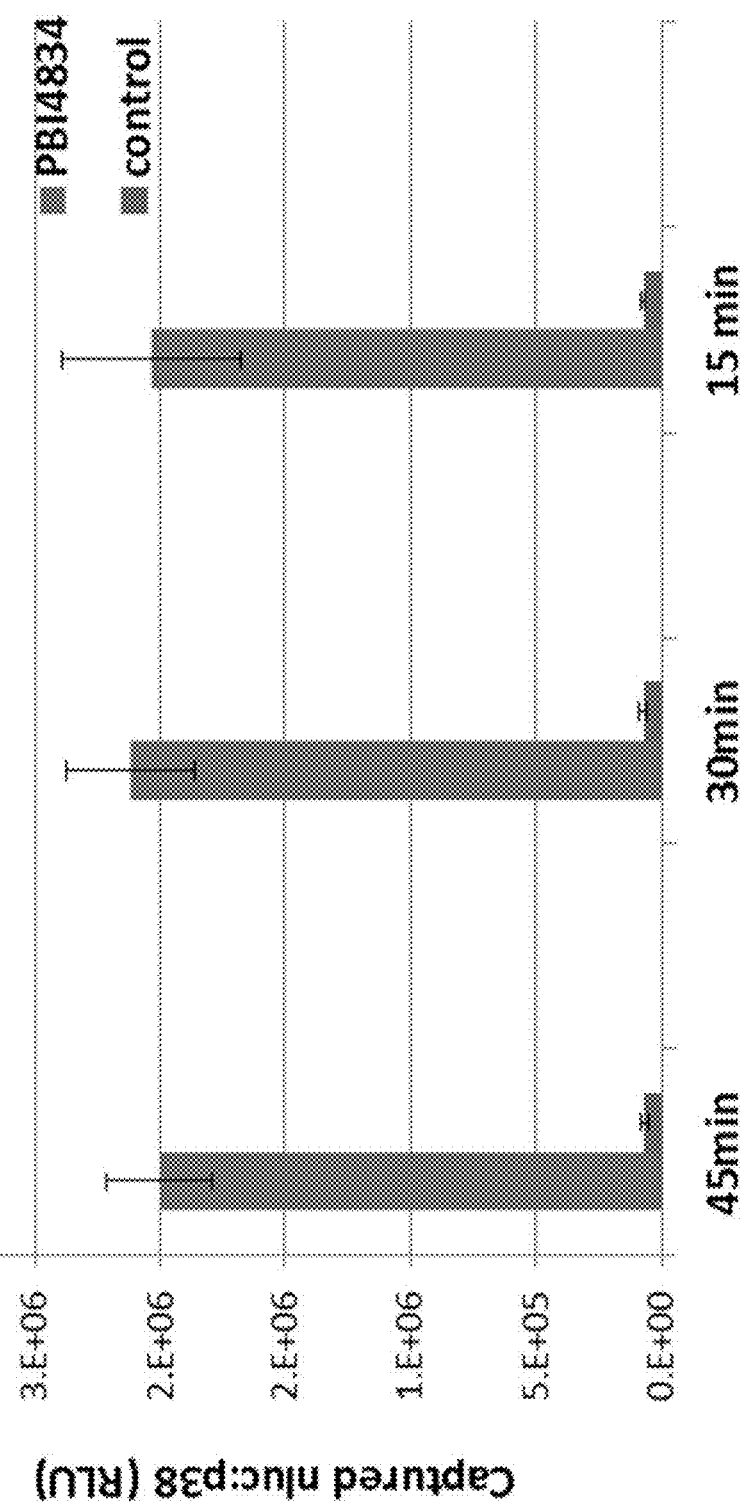
FIG. 5 shows a graph depicting the ability of embodiments of the present invention to capture target proteins that bind to drugs in a shor time span.

The high signal over background achieved within 15 minutes of capture on the HALOTAG protein beads demonstrates the efficiency of the capture method, and its ability to capture target proteins that bind to drugs with low to moderate affinity (FIG. 5). In this example, only 1% of the expressed fusion was specifically captured to the beads. However, because of the high sensitivity of the NANOLUC luciferase, the level of capture is more than ample for detection of specific capture over background.

Example 4

Experiments were conducted during development of embodiments of the present invention to demonstrate the advantage of a carbamate chloroalkane linker for pull-down of a target protein from cells onto HALOTAG protein beads using chloroalkane modified drugs. In this example, methotrexate-chloroalkane conjugates PBI-5015 (carbamate chloroalkane linker) and PBI-4848 (02 chloroalkane linker) were tested for their binding efficiency to HALOTAG protein in lysate, binding efficiency to DHFR in cells and ability to pull down a NANOLUC-DHFR fusion protein from living cells.

PBI-5015: Methotrexate Carbamate Chloroalkane

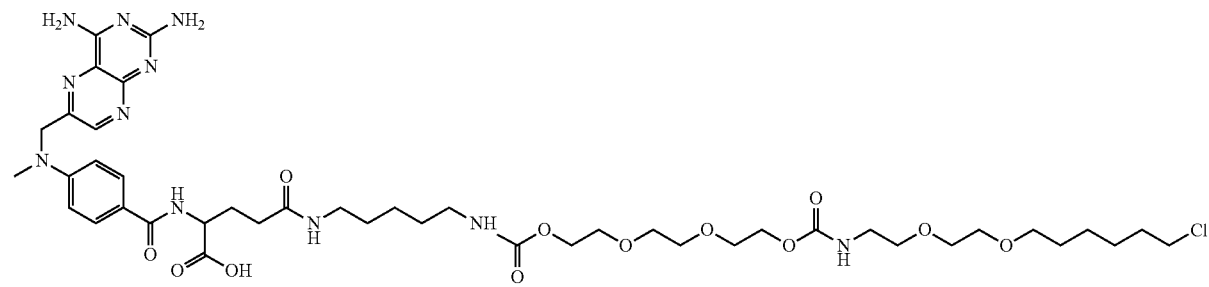 [SMILES: CN(Cc1cnc2nc(N)nc(N)c2n1)c1ccc(C(=O)NC(CCC(=O)NCCCCCNC(=O)OCCOCCOCCOC(=O)NCCOCCOCCCCCCCl)C(=O)O)cc1]

PBI-4848: Methotrexate-02 Chloroalkane

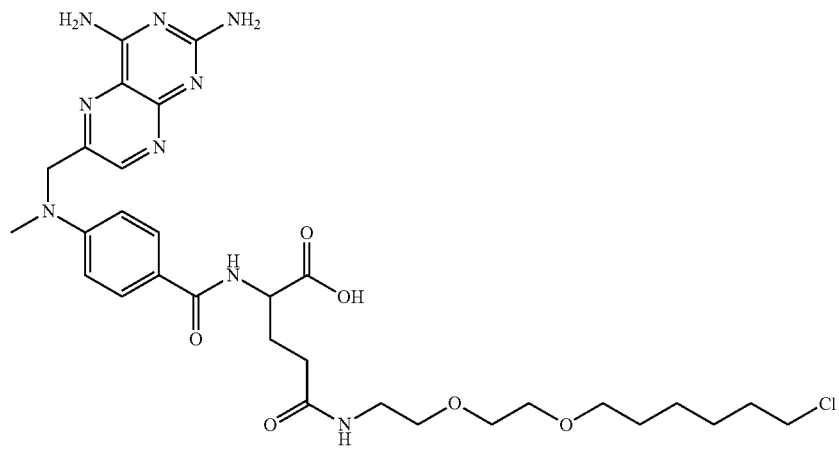 [SMILES: CN(Cc1cnc2nc(N)nc(N)c2n1)c1ccc(C(=O)NC(CCC(=O)NCCOCCOCCCCCCCl)C(=O)O)cc1]

Figure 6A:
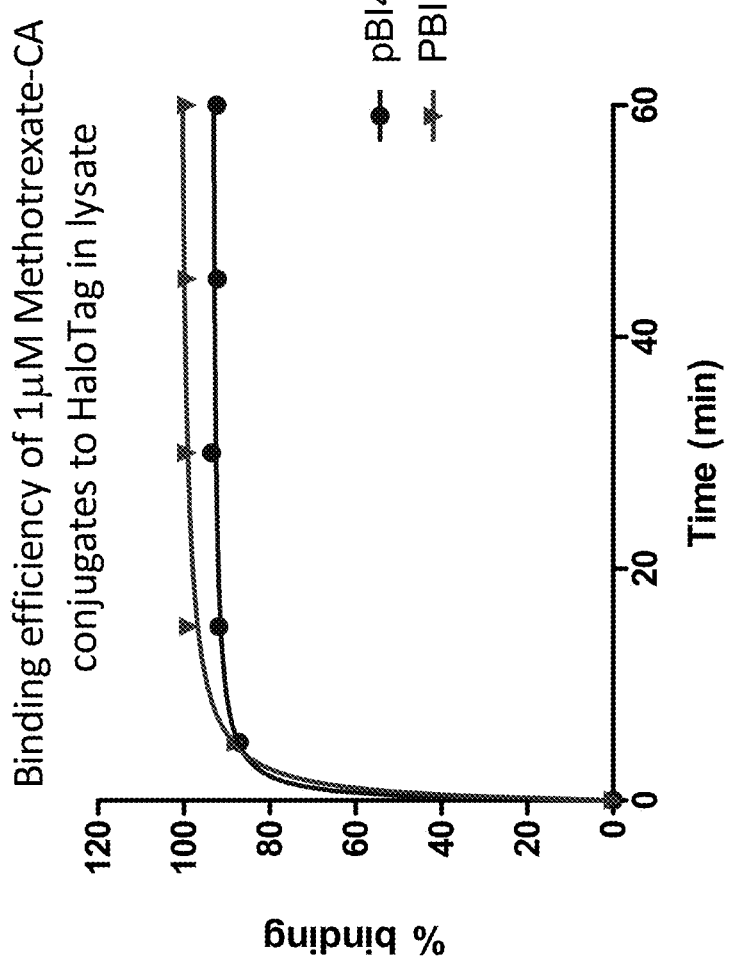
FIGS. 6A-C shows graphs depicting the use of a carbamate chloroalkane linker for pull-down of a target protein from cells using chloroalkane modified small molecules: (A) binding efficiency of methotrexate-CA conjugates to HALOTAG in cell lysate, (B) binding efficiency of methotrexate-CA conjugates to nluc:DHFR in live cells, and (C) effect of chloroalkane linker on capture of nluc:DHFR from HEK293 cells.

Binding efficiency to HALOTAG protein in lysate was measured by adding methotrexate-chloroalkane conjugates (final concentration 1 uM) to lysate from cells expressing a HALOTAG protein. Following 0-60 min binding, the reaction was chased with 1 μM fluorescent HALOTAG ligand. Unbound HALOTAG protein was detected through binding to the fluorescent HALOTAG ligand followed by analysis on a SDS-PAGE gel and detection on a fluorescent gel scanner. Results indicate that both linkers provide fast labeling kinetics to the HALOTAG protein (FIG. 6A).

Figure 6B:
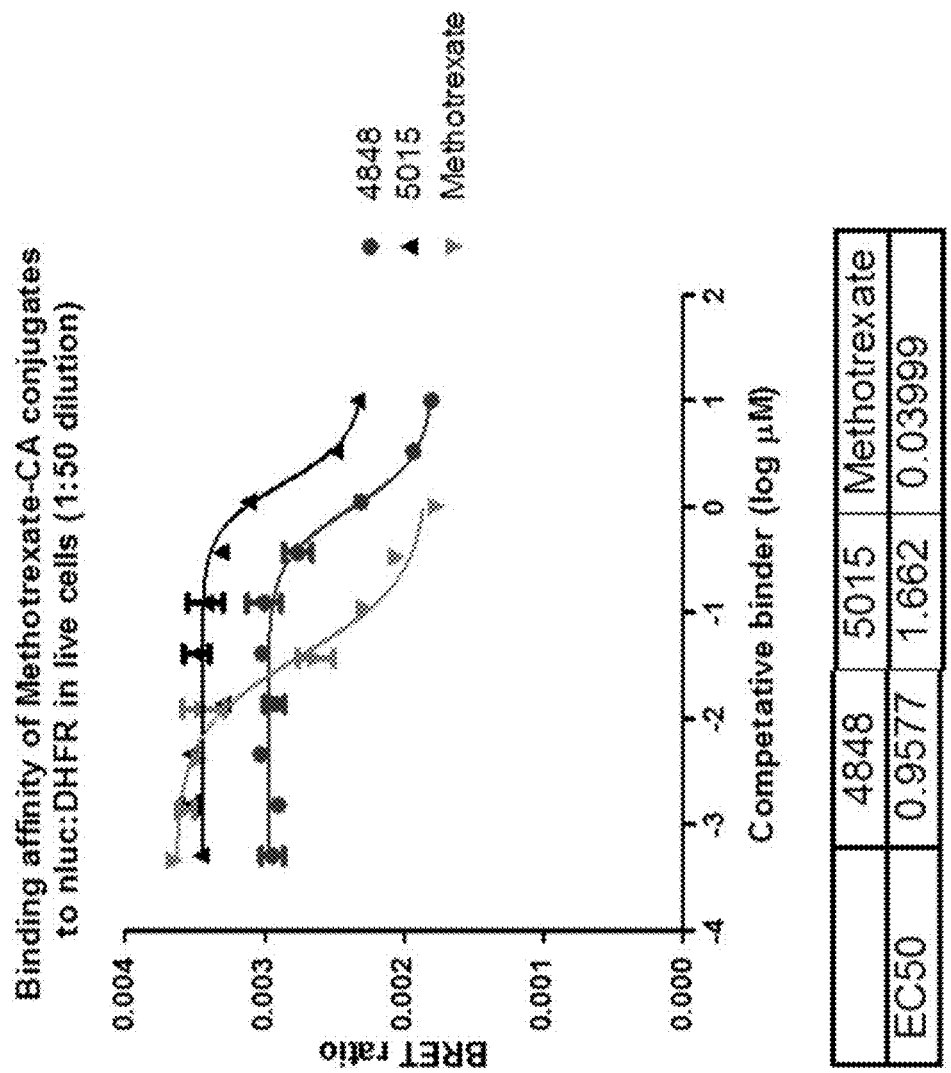

Binding affinity to DHFR in live cells was tested using BRET. HEK293 cells in wells of a 96-well plate were transfected using PEI with plasmid DNA encoding a NANOLUC-DHFR fusion. The DNA was diluted 1:50 with a promoterless carrier DNA plasmid (PSI) to a final concentration of 80 ng total DNA per well. Twenty-four hours post-transfection, cells were serum starved for additional 24 hours and then treated with serially diluted PBI-4848 or PBI-5015 in the presence of 1 μM PBI-4890 (TOM-methotrexate derivative). After two hours of equilibrium binding, furimazine (a coelenterazine derivative; Promega Corp.) was added to a final concentration of 20 μM, and BRET measured on a Varioskan luminometer. The dose-response BRET curves indicate that PBI-4848 has higher affinity to DHFR (FIG. 6B).

Figure 6C:
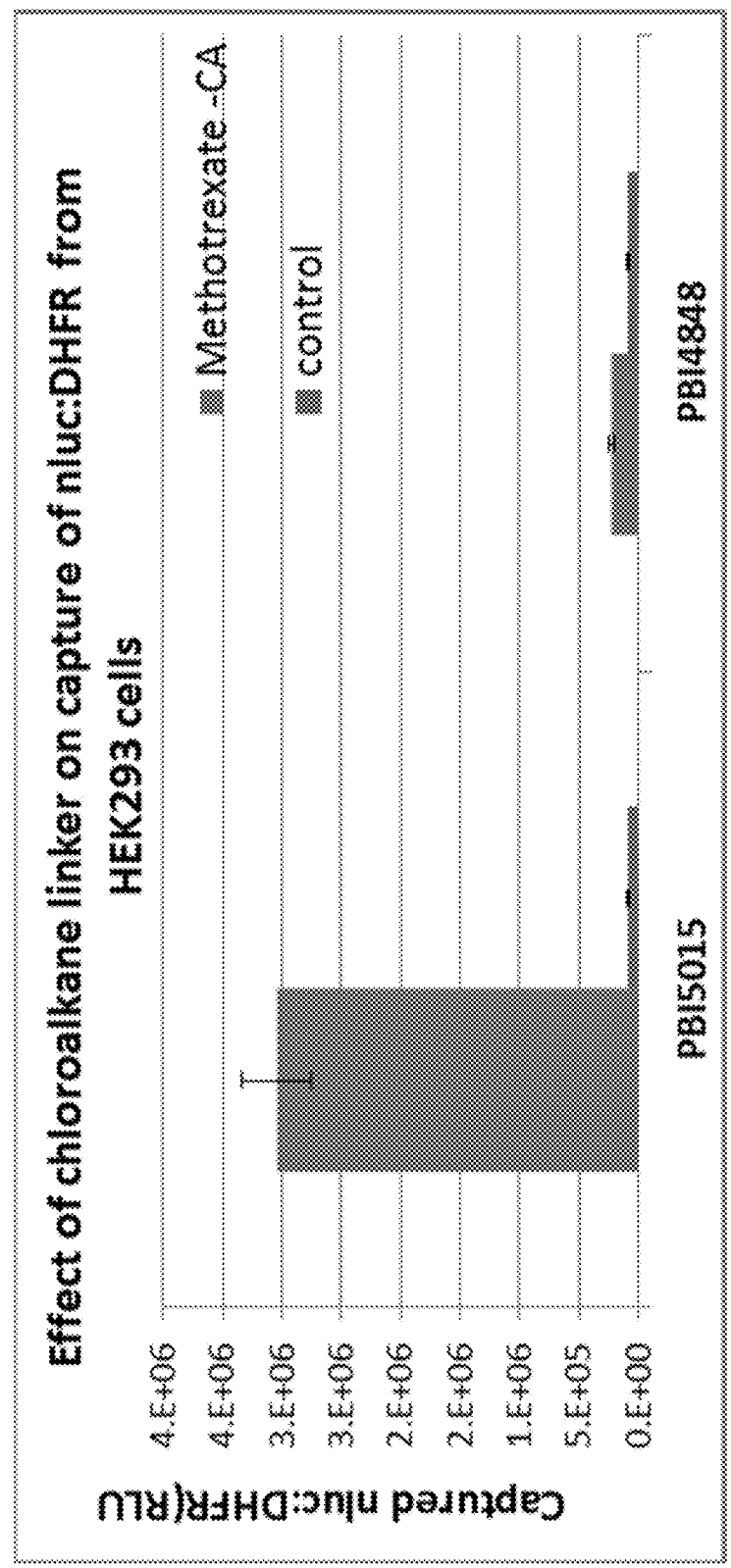

To demonstrate the ability to specifically pull down NANOLUC:DHFR (Nluc:DHFR) from live cells, HEK293 cells in wells of 96-well plate were transfected using PEI with plasmid DNA encoding NANOLUC-DHFR fusion. The DNA was diluted 1:50 with a promoterless carrier DNA plasmid (PSI) to a final concentration of 80 ng total DNA per well. Twenty-four hours post-transfection, cells were serum starved for additional 24 h and then incubated with 10 μM PBI-4848 or PBI-5015 while control cells were not treated with the conjugated drug. Following equilibration binding of 2 h, the media was removed, and the cells quickly washed with PBS and lysed in detergent-based lysis buffer for 10 min. Cell lysates were then transferred to wells of a 96-well plate containing 0.5 μl settled paramagnetic HALOTAG protein beads and incubated with shaking for 45 min. Following binding, the unbound fraction was removed, the HALOTAG protein paramagnetic beads washed, 150 μM unconjugated methotrexate added, and the captured NANOLUC:DHFR specifically released from the beads by competition with the unconjugated methotrexate for 60 min. The released NANOLUC:DHFR (+PBI5015 or +PBI 4848) and control samples were detected by NANOGLO luciferase detection reagent. Although both PBI-4848 and PBI-5015 have similar binding efficiency to HALOTAG, only PBI-5015 (which has lower affinity to DHFR) efficiently pulled down the Nluc:DHFR fusion, thus demonstrating the advantage of the carbamate linker in pull-down applications (FIG. 6C).

PBI-4890 Methotrexate-TOM

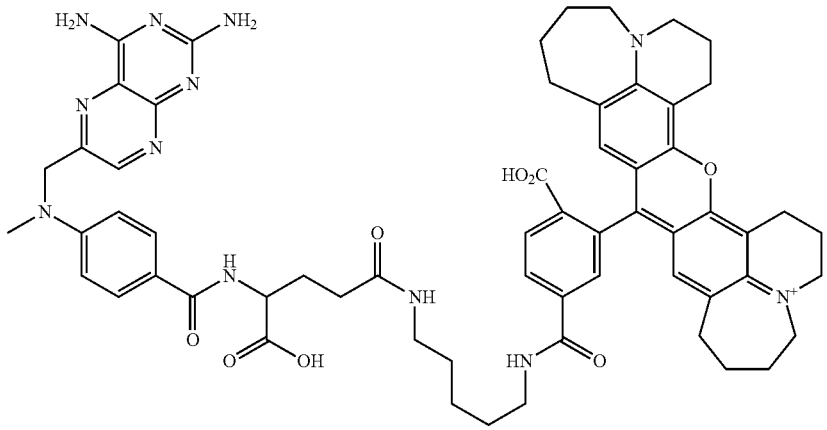 [SMILES: CN(Cc1cnc2nc(N)nc(N)c2n1)c1ccc(C(=O)NC(CCC(=O)NCCCCCNC(=O)c2ccc(C(=O)O)c(C3=c4cc5c6c(c4Oc4c3cc3c7c4CCCN7CCCC3)CCC[N+]=6CCCC5)c2)C(=O)O)cc1]

Example 5

Methods for specific release of a NANOLUC fusion protein from HALOTAG protein beads include, for example:
1. Competition with unconjugated bioactive agent;
2. Use of a bioactive agent tethered to a capture ligand (e.g., chloroalkane ligand) wherein the capture ligand contains a chemically-cleavable linker (e.g., chloroalkane linker) to allow fast release of the NANOLUC fusion protein;
3. Use of a capture ligand solid support (e.g., HALOLINK HALOTAG resin) wherein the linker attaching the capture ligand (HALOTAG ligand) to the solid support can be chemically cleaved allowing fast release of the capture protein-capture ligand-bioactive agent-cellular target complex (e.g., HALOTAG-chloroalkane-drug conjugate-NANOLUC fusion protein complex); and
4. Proteolytic cleavage of the cellular target from the reporter, e.g., NANOLUC fusion protein released the NANOLUC protein.

Experiments were conducted during development of embodiments of the present invention to demonstrate such methods for specific release of the NANOLUC fusion protein from HALOTAG protein beads. In this example, BIRB-chloroalkane conjugate (PBI-4834) and BIRB chloroalkane conjugate containing a cleavable linker (PBI-5131) were utilized to pull-down a NANOLUC-p38 alpha fusion protein from HEK293 cell lysates. Lysate of cells expressing NANOLUC-p38 fusion were incubated with 1 μM PBI-4834 or PBI-5131 (final concentration) while control lysates were not treated with the conjugated drugs. Following equilibration binding for 2 h, the lysates were transferred to wells of a 96-well plate containing 0.5 μl settled paramagnetic HALOTAG protein beads and incubated with shaking for 45 min. Following binding the unbound fraction was removed, the HALOTAG protein paramagnetic beads were washed 3×, and the captured NANLUC-p38 alpha fusion specifically released from the beads by one of two methods:
1. 150 μM unconjugated BIRB796 was used to compete for binding with the conjugated BIRB796 on the NANOLUC-p38 alpha fusion for 60 min.
2. The NANOLUC-p38 alpha fusion was rapidly released through 10 min chemical cleavage of the chloroalkane linker with 10 mM of sodium hydrosulfite (PBI-5131 is a chloroalkane cleavable linker).

Figure 7:
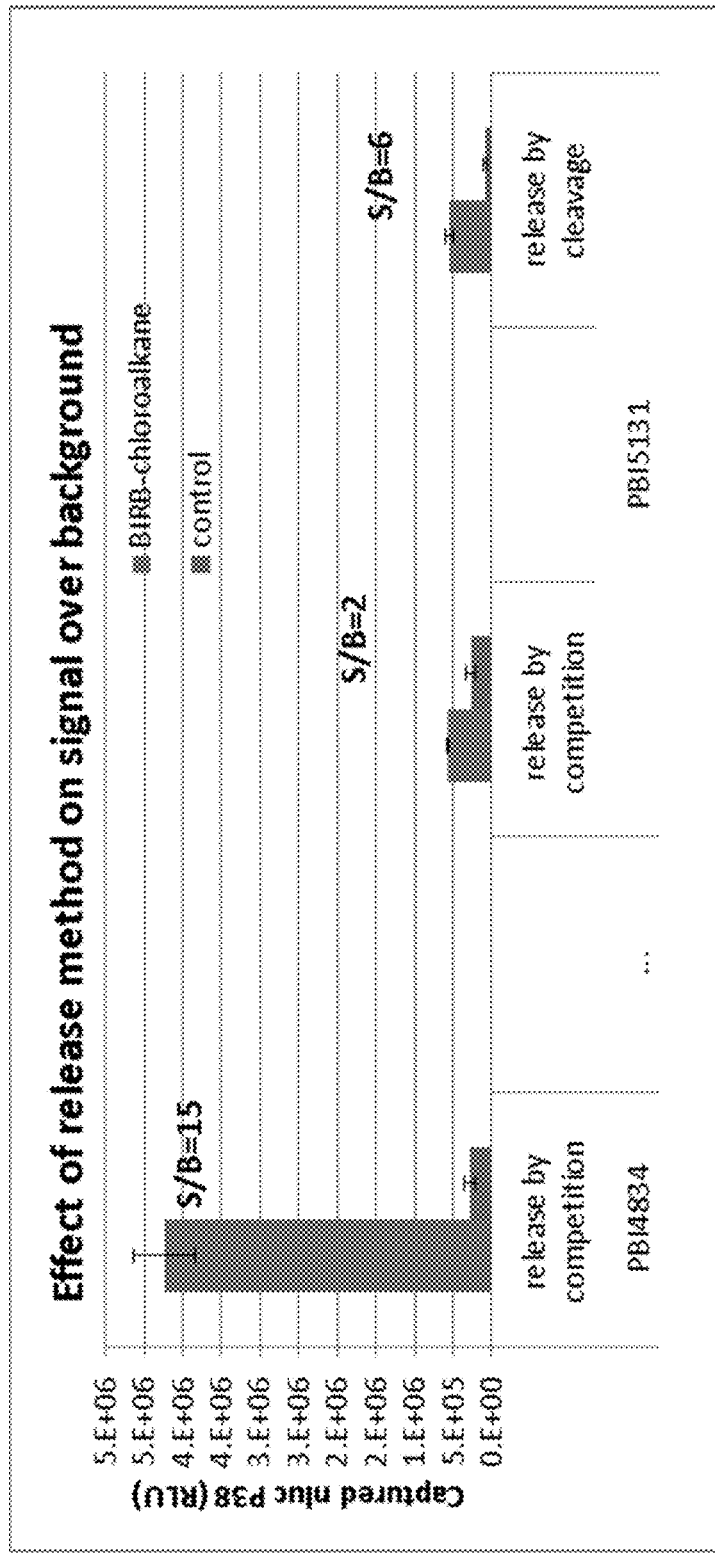
FIG. 7 shows a graph depicting the effect of various release methods on signal-over-background.

The released NANOLUC-p38 alpha (+PBI4834/+PBI5131) and control (− drug) were detected with NANO-GLO luciferase detection reagent. Although the pull-down efficiency with PBI-4834 (carbamate linker) is significantly higher compared to PBI-5131, this example demonstrates the benefit of rapid release using chemical cleavage for minimizing background leading to significant increase in specific capture (FIG. 7).

Example 6

The following provides synthesis schemes for exemplary compounds that find use in embodiments of the present invention.

PBI-4848: Methotrexate-O2 Chloroalkane

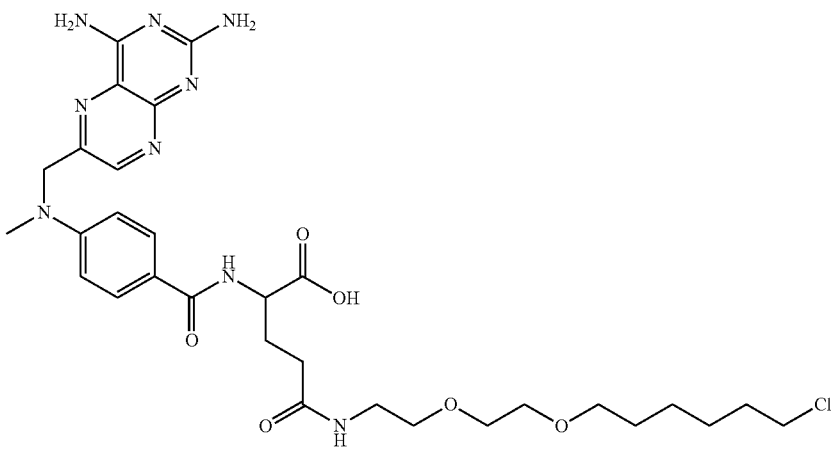 [SMILES: CN(Cc1cnc2nc(N)nc(N)c2n1)c1ccc(C(=O)NC(CCC(=O)NCCOCCOCCCCCCCl)C(=O)O)cc1]

50 mg of methotrexate hydrate was stirred in 3 mL of DMF and treated with EDAC (63 mg, 330 umol) and triethylamine (77 uL, 550 umol). After 10 min, 12-chloro-3,6-dioxo-dodecylamine hydrocholide (21.5 mg, 83 umol) was added. After 3 h, the product was isolated by preparative HPLC (2→50% MeCN in 0.1% aqueous formic acid). The appropriate fractions were concentrated and lyophilized to yield an orange solid. Calculated for M+H: 660.3; found 660.7.

Methotrexate Pentylamine Intermediate

To a mixture of methotrexate hydrate (50 mg, 110 umol), EDAC (63 mg, 330 umol) and triethylamine (77 uL, 550 umol) in 2 mL of DMF, N-Boc cadaverine (22 mg, 110 umol) was added. The reaction was stirred for 90 min then quenched with 2 mL of 1 N HCl diluted with water and subjected to preparative HPLC (20→50% MeCN in 0.1% aqueous formic acid). The appropriate fractions were concentrated and lyophilized to yield the desired product. Calculated for M+H: 639.3; found 639.5.

Methotrexate N-Boc-cadaverine adduct (24 mg, 38 umol) was treated with 4 M HCl in dioxane (0.5 mL) at RT. Upon completion of the reaction, the solvents were removed under reduced pressure, and the resulting residue was stirred with diethyl ether to form a yellow precipitate which was isolated by centrifugation. The hydrochloride salt was used without further characterization.

PBI-5015 Methotrexate Carbamate Chloroalkane

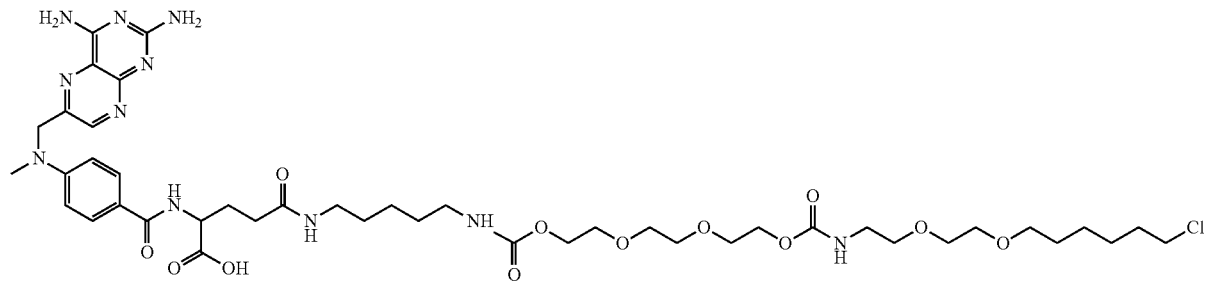 [SMILES: CN(Cc1cnc2nc(N)nc(N)c2n1)c1ccc(C(=O)NC(CCC(=O)NCCCCCNC(=O)OCCOCCOCCOC(=O)NCCOCCOCCCCCCCl)C(=O)O)cc1]

Methotrexate hydrate pentylamine HCl salt (8 mg, 14 umol) was combined with 2-(2-(2-(((4-nitrophenoxy)carbonyl)oxy)ethoxy)ethoxy)ethyl, (2-(2-((6-chlorohexyl)oxy)ethoxy)ethylcarbamate (12 mg, 21 umol) and triethylamine in 2 mL DMF. After 2 h, the reaction was quenched by addition of 1 N HCl, and the product was isolated by preparative HPLC eluting with 10→50% MeCN in aqueous 0.1% formic acid. After concentration, the resulting yellow solid was taken up in DCM and washed with saturated $NaHCO_3$. Evaporation of the organic layer yielded 1.9 mg of a yellow solid. Calculated for M+H: 964.5, found 964.5.

PBI-4890 Methotrexate-TOM

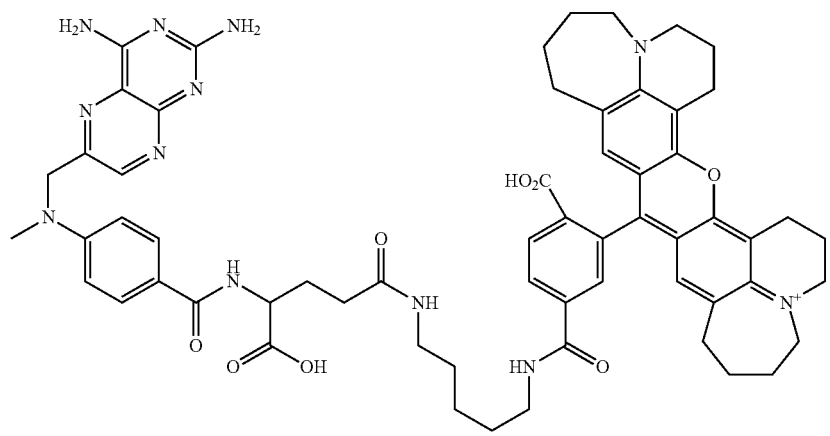 [SMILES: CN(Cc1cnc2nc(N)nc(N)c2n1)c1ccc(C(=O)NC(CCC(=O)NCCCCCNC(=O)c2ccc(C(=O)O)c(C3=c4cc5c6c(c4Oc4c3cc3c7c4CCCN7CCCC3)CCC[N+]=6CCCC5)c2)C(=O)O)cc1]

Methotrexate hydrate pentylamine hydrochloride salt (6 mg, 10 umol) was combined with 5.4 mg of TOM succinimidyl ester (8.2 umol) in 1 mL of DMF, and 5 drops of TEA were added. After 45 min, the reaction was diluted with $H_2O$ and MeCN and subjected to preparative HPLC (25→75% MeCN in 0.1% aqueous formic acid) followed by lyophilization to yield 6 mg of a blue solid. Calculated for M+H: 1083.5; found 1083.5.

BIRB Cleavable Linker Chloroalkane PBI 5131

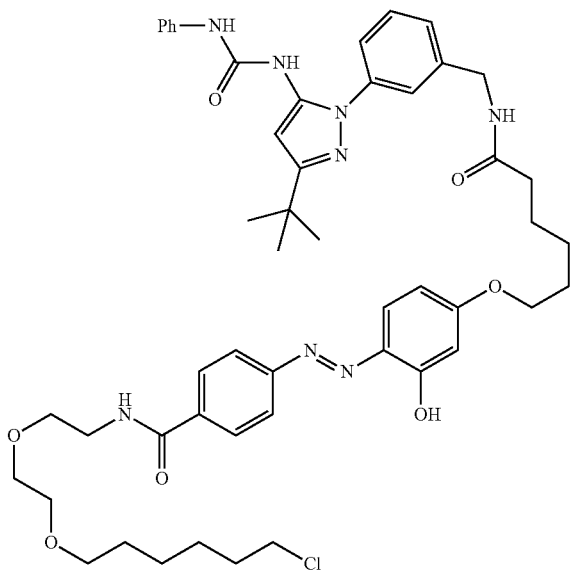 [SMILES: CC(C)(C)c1cc(NC(=O)Nc2ccccc2)n(-c2cccc(CNC(=O)CCCCCOc3ccc(/N=N/c4ccc(C(=O)NCCOCCOCCCCCCCl)cc4)c(O)c3)c2)n1]

Resorcinol (3.31 g, 30 mmol) was dissolved in 10 mL of DMF, and K$_2$CO$_3$ (3.32 g, 24 mmol) added. The mixture was stirred until all solid had dissolved, and the reaction turned a dark brown. 6-Bromohexanoate ethyl ester (4.69 g, 21 mmol) was added all at once, the reaction stirred overnight, and then poured into 1 M HCl and extracted with 3×50 mL EtOAc. The combined organic layers were washed with brine, then adsorbed onto Celite and subjected to column chromatography eluting with 0→50% EtOAc in heptanes. Calculated for M+H: 254.1; found 253.8.

Ethyl 6-(3-hydroxyphenoxy)hexanoate (0.96 g, 3.8 mmol) was dissolved in a mixture of MeOH and H2O, and LiOH hydrate (639 mg, 15.2 mmol) added. After 2 h, the reaction was concentrated under reduced pressure and then acidified with 1 M HCl to give a white precipitate, which yielded 550 mg of a white solid after filtration and drying under vacuum. Calculated for M+H: 225.1; found 225.2

Ethyl 4-aminobenzoate (405 mg, 2.45 mmol) was stirred in 7.7 mL of a mixture of acetone/2 N HCl in an ice bath. A solution of sodium nitrite (215 mg, 3.12 mmol) dissolved in 8 mL of H$_2$O was added dropwise over 10 min, and the reaction was stirred for an additional 20 min. The reaction was then added dropwise over 20 min to a stirred solution of 6-(3-hydroxyphenoxy)hexanoate in 18 mL of 1 N NaOH in an ice bath, generating a dark red color. Stirring and cooling was continued for 40 min, and the reaction was then neutralized with 1 N HCl and diluted with water. The resulting brown precipitate was collected by filtration and directly carried on to the next step.

To a solution of the carboxylic acid from the previous step (50 mg, 0.12 mmol) in DMF (4 mL), 1-(1-(4-(aminomethyl)phenyl)-3-tertbutyl-1H-pyrazol-5-yl)-3-(naphthalen-1-yl)urea (50 mg, 0.14 mmol), ethyl dimethylaminopropylcarbodiimide (EDAC, 30 mg, 0.16 mmol) and 1-hydroxybenzotriazole (HOBt, 22 mg, 0.16 mmol) was added. After stirring for 40 h, the reaction was partitioned between EtOAc and NaHCO$_3$ (sat. aq.), the layers separated and the organic layer washed with water and NaCl (sat. aq.), dried and concentrated. The resulting red solid was purified by preparative HPLC (10%→100% ACN in 0.1% aqueous TFA) and subsequent concentration yielded 44 mg of an orange solid. Calculated for M+H: 745, found 745.

To a solution of the ester from the previous reaction (44 mg, 0.06 mmol) in THF (3 mL), NaOH (1N, 1 mL) was added. After stirring for 8 days, the reaction was acidified and purified by preparative HPLC (10%→100% ACN in 0.1% aqueous TFA) and subsequently concentrated to yield 25 mg of an orange solid. Calculated for M+H: 717, found 717.

To a solution of the carboxylic acid (14 mg, 0.02 mmol) from the previous reaction in DMF (2 mL), N,N,N',N'-Tetramethyl-O—(N-succinimidyl)uronium tetrafluoroborate (TSTU, 12 mg, 0.04 mmol) and diisopropylethylamine (17 μL, 0.1 mmol) was added. After stirring for 30 min, 2-[2-(6-chloro-hexyloxy)-ethoxy]-ethylammonium hydrochloride (Promega, 10 mg, 0.04 mmol) was added. After stirring for 36 h, the reaction was acidified and purified by preparative HPLC (10%→100% ACN in 0.1% aqueous TFA) and subsequently concentrated to yield 25 mg of PBI 5131 as an orange solid. Calculated for M+H: 923, found 923.

BIRB Carbamate Chloroalkane PBI 4834

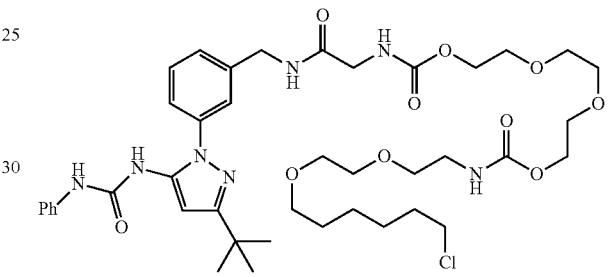

1-(1-(4-((2-aminoacetamido)methyl)phenyl)-3-tert-butyl-1H-pyrazol-5-yl)-3-phenylurea (10 mg, 18 umol) was combined with 2-(2-(2-(((4-nitrophenoxy)carbonyl)oxy)ethoxy)ethoxy)ethyl (2-(2-((6-chlorohexyl)oxy)ethoxy)ethylcarbamate (12 mg, 21 umol) and diisopropylethylamine (0.01 mL, 0.06 mmol) in 2 mL DMF. After 2 h, the reaction was quenched by addition of 1 N HCl, and the product was isolated by preparative HPLC eluting with 10→100% MeCN in aqueous 0.1% trifluoroacetic acid. Evaporation of the organic layer yielded 1.9 mg of a yellow solid. Calculated for M+: 846, found 846.

Boc-Protected SAHA Amine

7-Trityloxycarbamoyl heptanoic acid (Schaefer et al. Med Chem Lett 2008, 16, 2011-2033; herein incorporated by reference in its entirety) (200 mg, 463 umol) was combined with 4-[(N-Boc)aminomethyl]aniline (113 mg, 510 umol), HBTU (352 mg, 927 umol) and triethylamine (194 uL, 1.4 mmol) in 3 mL of DMF. The reaction was stirred overnight, then adsorbed onto Celite, and the product was obtained by column chromatography eluting with a gradient of 0→100% EtOAc in heptanes. Calcd for M+H: 635.3; found 635.9.

SAHA Amine

Suberoyl(4-[(N-Boc)aminomethyl]anilide) hydroxamic acid (286 mg, 450 mmol) was dissolved in 2 mL of DCM to which 0.25 mL of TIS was added. Trifluoroacetic acid (0.9 mL) was then added, and the reaction was stirred for 30 min. Solvents were removed under reduced pressure, and the crude reaction product could be purified by preparative HPLC or used without further purification.

SAHA-Carbamate (SAHA-Chloroalkane) PBI 5040

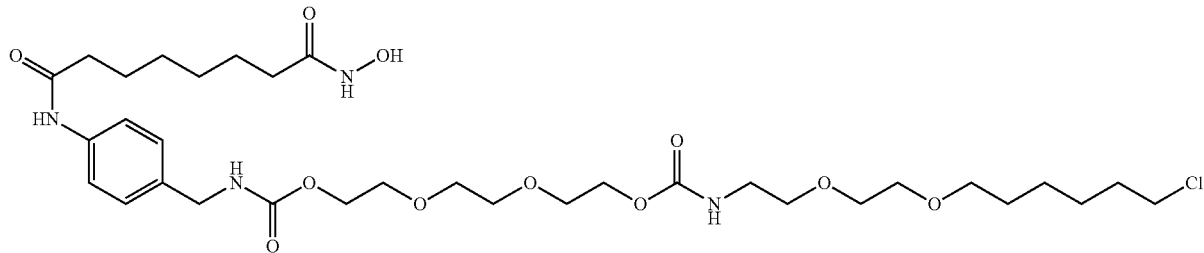 [SMILES: O=C(CCCCCCC(=O)Nc1ccc(CNC(=O)OCCOCCOCCOC(=O)NCCOCCOCCCCCCCl)cc1)NO]

Suberoyl[4-(aminomethyl)anilide] hydroxamic acid TFA salt (9 mg, 22 umol) was stirred in 1 mL of DMF with 1 drop of TEA. A 13-mg portion of 2-(2-(2-(((4-nitrophenoxy)carbonyl)oxy)ethoxy)ethoxy)ethyl (2-(2-((6-chlorohexyl)oxy)ethoxy)ethylcarbamate (23 umol) in 0.5 mL of DMF was then added. After 90 min, the reaction was quenched by addition of $H_2O$ and acidified with a small amount of TFA, and the desired product was isolated by preparative HPLC eluting with 5→60% MeCN in 0.1% aqueous TFA. Calcd for M+H: 719.4; found 719.

SAHA-Biotin PBI 5474

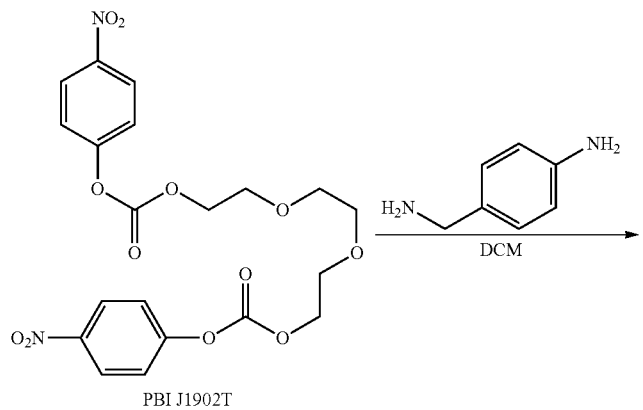

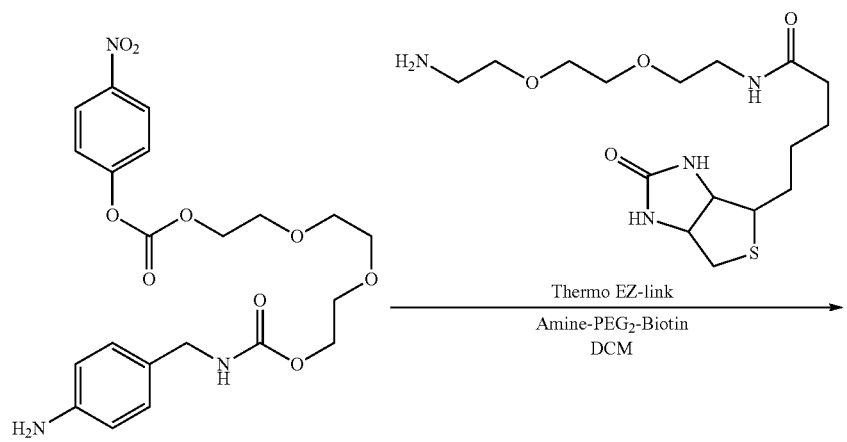

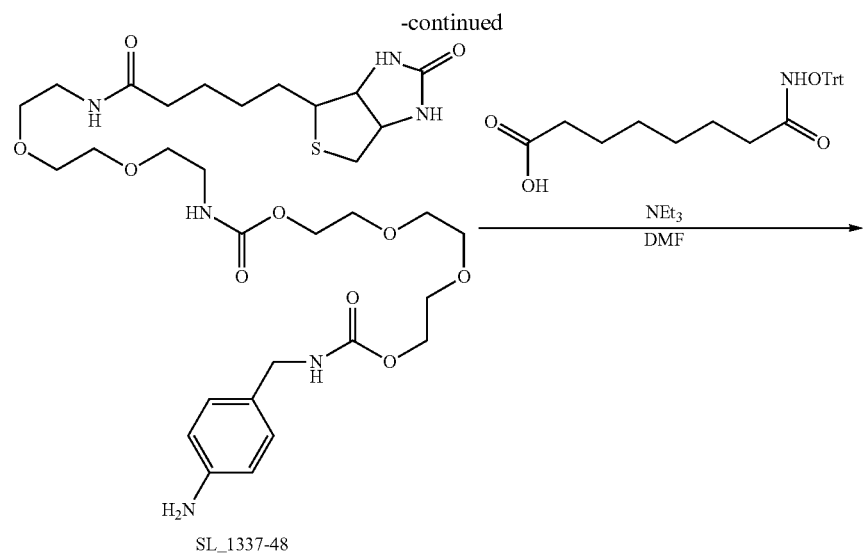
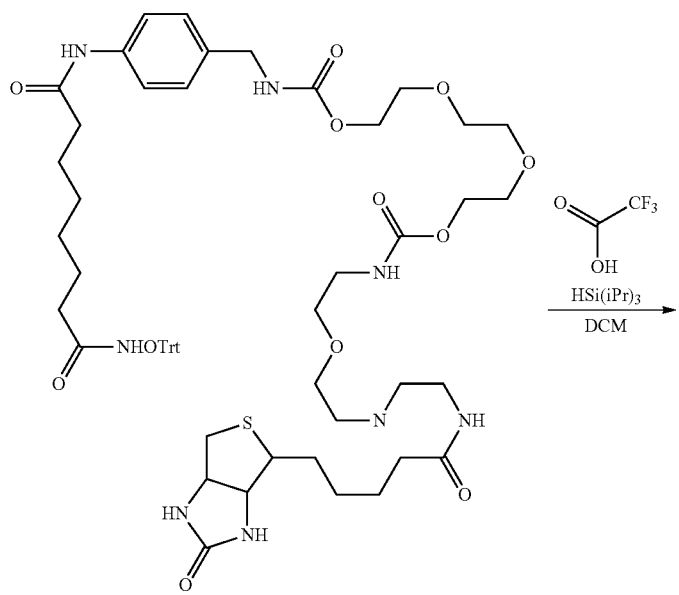

-continued

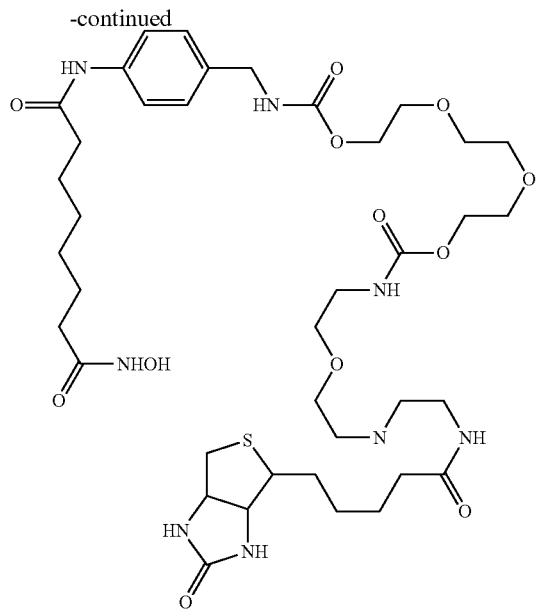

SL_1337-57

To a solution of bis-carbamate, "PBI J1902T" (50.0 mg, 104 μmol) in dichloromethane (5 mL) and a solution of 4-(aminomethyl)aniline (3.8 mg, 31 μmol) in dichloromethane (5 mL) was slowly (over 10 minutes) added. Upon completion of the addition, the resulting yellow solution was left at 22° C. for 12 hours. The reaction mixture was purified by silica gel chromatography (0→5% MeOH/DCM) to provide 8.0 mg (55% yield) of carbamate SL_1337_39 as a yellow oil. $^1$H NMR (300 MHz, CDCl$_3$) 8.26 (d, J=9.1, 2H), 7.36 (d, J=9.1, 2H), 7.05 (d, J=8.3, 2H), 6.64 (d, J=8.3, 2H), 5.06 (s, 1H), 4.51-4.35 (m, 2H), 4.27-4.20 (m, 4H), 3.87-3.74 (m, 2H), 3.74-3.53 (m, 6H) 1; HRMS (SI) calc'd for $C_{21}H_{26}N_3O_9^+$ [M+H]$^+$ 464.17, found 464.35.

To a solution of SL_1337-39 (8.0 mg, 17 μmol) in dichloromethane (5 mL), a solution of "Thermo EZ-Link Amine-PEG2-Biotin" (7.1 mg, 19 μmol) in DMF (5 mL) was added. The clear yellow reaction was stirred at 22° C. for 20 hours, at which point LCMS analysis indicated full consumption of starting material. The reaction was concentrated in vacuo, and the residue was dissolved in 5 mL DCM and purified by silica gel chromatography (0→30% MeOH/DCM) to provide 12.0 mg (99% yield) of aniline SL_1337-49 as a clear oil. HRMS (SI) calc'd for $C_{31}H_{51}N_6O_{10}S^+$ [M+H]$^+$ 699.34, found 699.48.

To a solution of SL_1337-49 (12.0 mg, 17 μmol) in DMF (2 mL), a solution of 8-oxo-8-((trityloxy)amino)octanoic acid (7.4 mg, 17 μmol), HATU (8.0 mg, 21 μmol) and NEt3 (8.7 mg, 86 μmol) in DMF (1 mL) was added. The clear yellow reaction was stirred at 22° C. for 17 hours, at which point LCMS analysis indicated full consumption of starting material. The reaction was concentrated in vacuo, and the residue was dissolved in 5 mL DCM and purified by silica gel chromatography (0→30% MeOH/DCM) to provide 11.5 mg (60% yield) of anilide SL_1337-53 as a clear oil. HRMS (SI) calc'd for $C_{58}H_{78}N_7O_{13}S^+$ [M+H]$^+$ 1112.54, found 1112.61.

To a solution of SL_1337-53 (11.5 mg, 10 μmol) in DCM (1 mL), triisopropylsilane (81.9 mg, 517 μmol) followed by TFA (25 μL) was added. The reaction was stirred at 22° C. for 20 minutes, at which point TLC analysis indicated full consumption of starting material. The reaction was concentrated in vacuo, and the residue was purified by preparative HPLC (3→95% MeCN/H$_2$O w/0.1% TFA over 45 minutes) to provide 9 mg (100% yield) of hydroxamic acid SL_1337-57 as white solids after lyophilization. HRMS (SI) calc'd for $C_{39}H_{64}N_7O_{13}S^+$ [M+H]$^+$ 870.43, found 870.48.

The following references are related to one or more of the above synthesis schemes and are herein incorporated by reference in their entireties: Hong et al. Am J Transl Res 2011, 3, 392; Murakata et al. U.S. Pat. No. 5,344,926 Sep. 6, 1994; Tecle et al. J. M. Chem Biol Drug Des 2009, 74, 547-549; Hong et al. Am J Transl Res 2011, 3, 392; $^1$J. Med. Chem. 2002, 45, 3296-3309.

Example 7

Endogenous Target Pull-Down (PBI-5015)

The following example demonstrates the ability of the chloroalkane-drug conjugate to isolate, e.g., pull-down, endogenous targets from cells.

HEK293 cells were plated into wells of a 6-well plate ($2.5 \times 10^5$ cells/well). 48 hours post plating, a final concentration of 10 uM of Methotrexate chloroalkane (PBI-5015) was added to 2 wells while control cells were not treated with the drug conjugate. Following equilibrium binding for 2 h, the media was removed, and the cells quickly washed with PBS and lysed in detergent-based lysis buffer for 10 min. Cell lysates were then transferred to an Eppendorf® tube containing 12.5 ul of settled paramagnetic HALOTAG protein beads and incubated with shaking for 15 min. Following binding, the unbound fraction was removed, the HALOTAG paramagnetic beads washed 3×, and the captured targets specifically released from the beads by competition with 150 μM unconjugated methotrexate for 60 mins. The released targets were subjected to mass spec analysis as well as western blot analysis using an anti-DHFR antibody (Sigma).

Figure 8A:
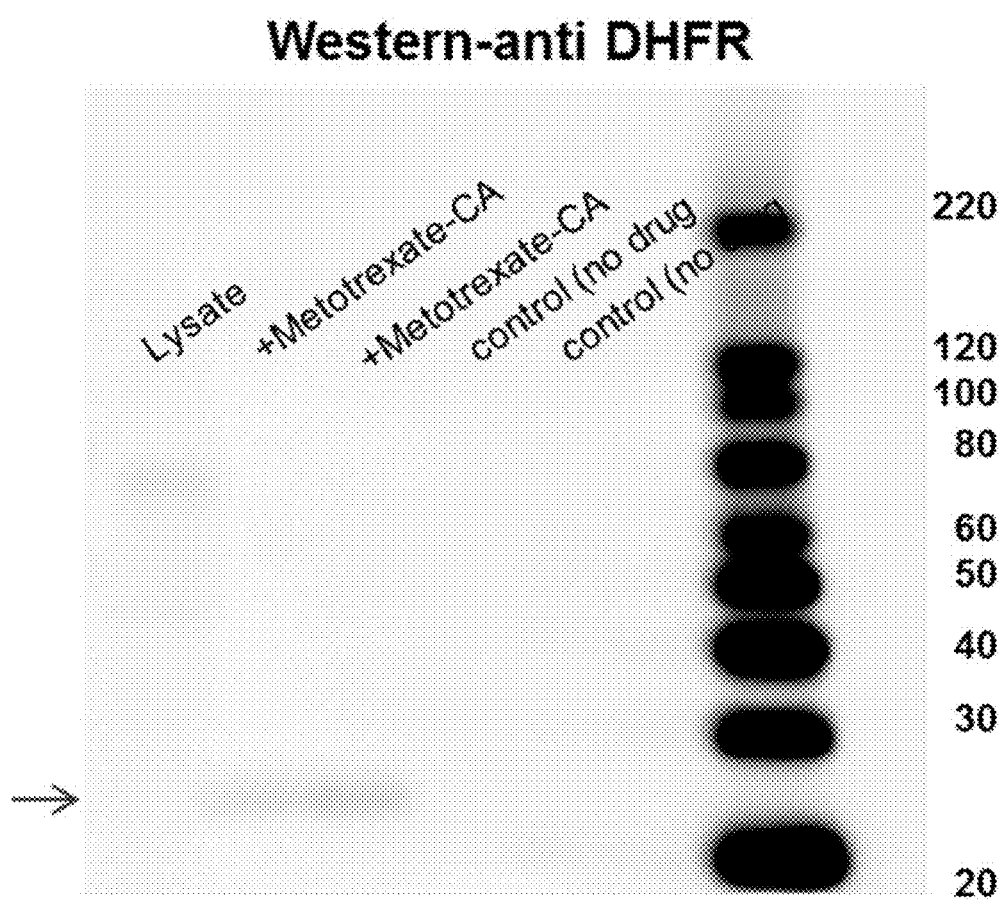
Figure 9A:
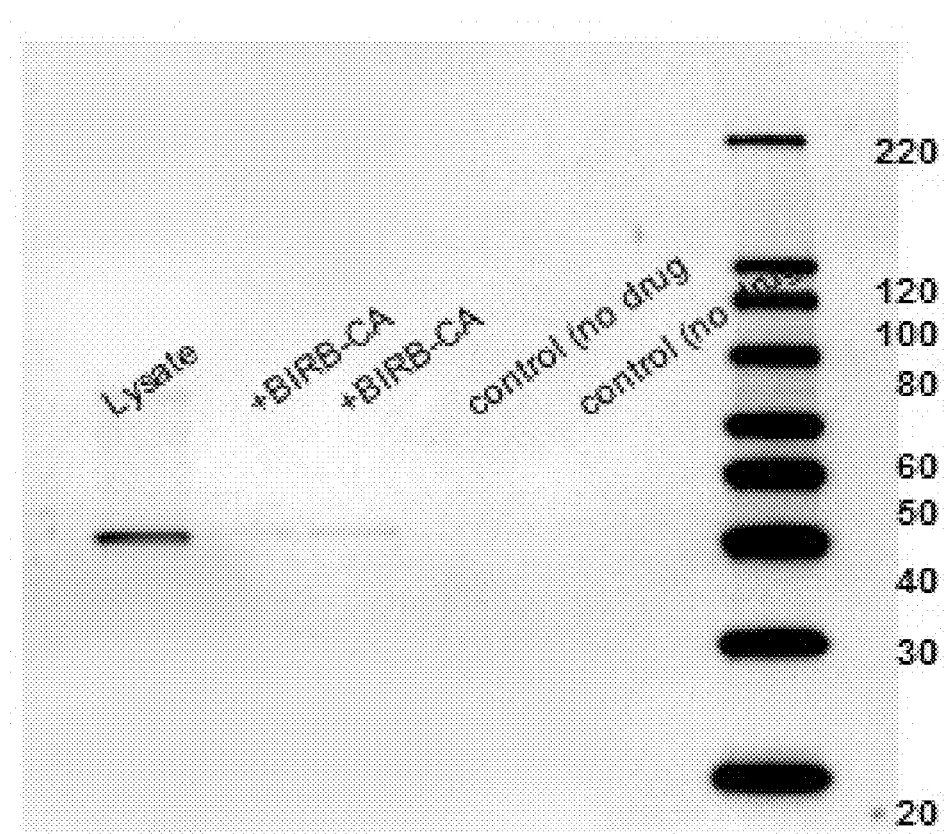

Results in FIG. 1A demonstrate that DHFR, a known target of methotrexate, can be specifically isolated, e.g., pulled down from the cells. Furthermore, although the expression level of DHFR in the cells is very low (not detected in lysate by western blot analysis), it was still efficiently captured as indicated by the western blot analysis (FIG. 8A) and mass spec analysis (FIG. 8B). In addition, the mass spec data indicates that with this method has very low background.

in FIG. 9A indicates that p38 alpha, a known target of BIRB796, can be specifically isolated, e.g., pulled down, from t cells as indicated by the western blot analysis (FIG. 2A) and mass spec analysis (FIG. 9B). In addition, the mass spec data indicates that with this method has very low background.

Example 8

Endogenous Target Pull-Down (PBI-4834)

The following example demonstrates the ability of the chloroalkane-drug conjugate to isolate, e.g., pull-down, endogenous targets from cells.

Example 9

Coupling HALOTAG Protein to Paramagnetic Beads

A. Synthesis of Step 4 Paramagnetic Resin

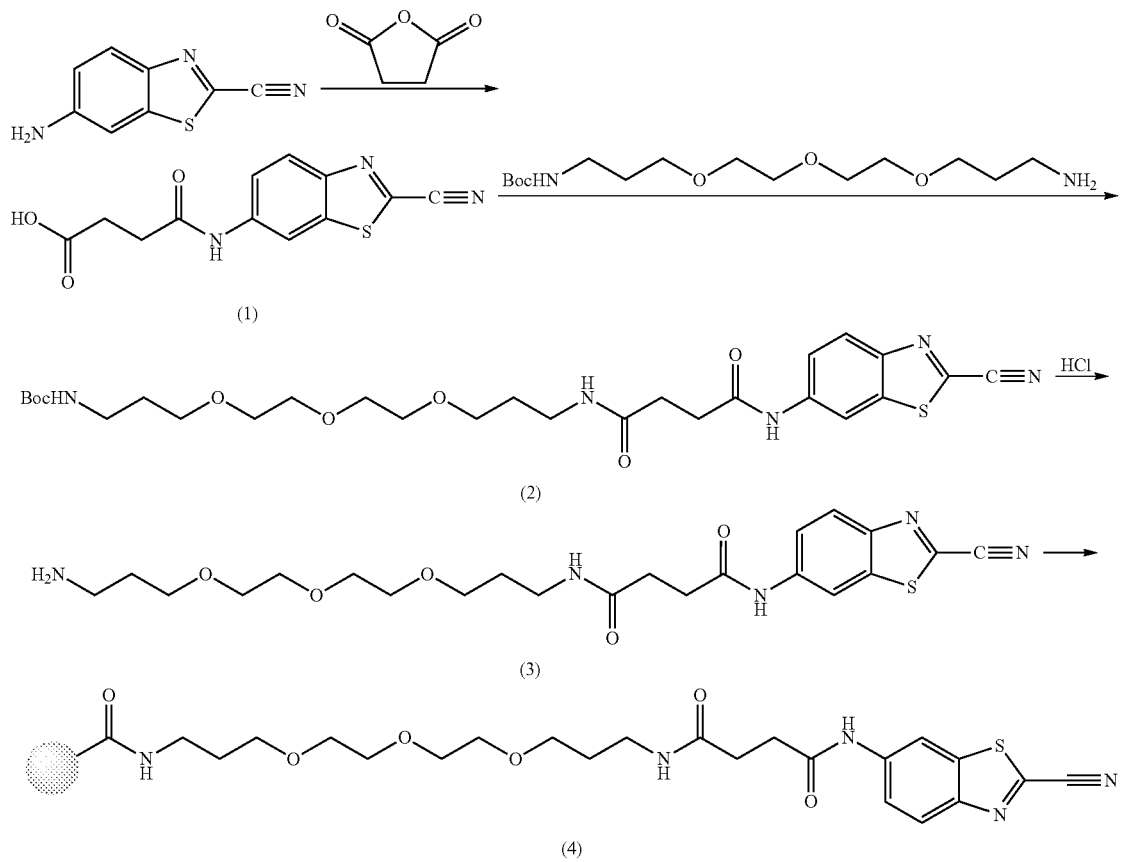

HEK293 cells were plated in a 6 well plate (2.5×10⁵ cells). 48 hours post plating, a final concentration of 10 uM of BIRB-chloroalkane (PBI-4834) was added to 2 wells while control cells were not treated with the drug conjugate. Following equilibrium binding for 2 h, the media was removed, and the cells were quickly washed with PBS and lysed in detergent-based lysis buffer for 10 min. Cell lysates were then transferred to an Eppendorf® tube containing 12.5 ul of settled paramagnetic HALOTAG protein beads and incubated with shaking for 15 min. Following binding, the unbound fraction was removed, the HALOTAG protein paramagnetic beads washed 3×, and the captured targets specifically released from the beads by competition with 150 µM unconjugated BIRB796 for 60 min. The released targets were subjected to mass spec analysis as well as western blot analysis using an anti-p38 alpha antibody (Abcam). Results 4-((2-cyanobenzo[d]thiazol-6-yl)amino)-4-oxobutanoic acid (1)

6-aminobenzo[d]thiazole-2-carbonitrile (2.0 g, 11.4 mmol), succinic anhydride (1.3 g, 13 mmol) and THF (15 mL) were placed in a 25 mL vessel and heated in a microwave synthesizer for 90 minutes at 110° C. Upon cooling, the reaction mixture was triturated with Et$_2$O and filtered, dried and evaporated to give 3.1 g of the product as a light yellow solid (99%). 1H-NMR (d6-DMSO, 300 MHz): δ 12.15 (s, 1H), 10.45 (s, 1H), 8.71 (s, 1H), 8.16 (d, 1H, J=8.2 Hz), 7.70 (d, 1H, J=8.2 Hz), 2.62 (m, 2H), 2.55 (m, 2H). ESI-MS: Calc. C12H10N3O3S+: m/z 276.3; found m/z 276.

tert-butyl (18-((2-cyanobenzo[d]thiazol-6-yl)amino)-15,18-dioxo-4,7,10-trioxa-14-azaoctadecyl)carbamate (2)

Compound 1 (4.93 g, 17.9 mmol), tert-butyl (3-(2-(2-(3-aminopropoxy)ethoxy)ethoxy)propyl)carbamate (7.40 g, 23.1 mmol) and DCM:DMF (10:1, 100 mL) were stirred together in a 250 mL round bottomed flask at room temperature. EDAC (4.0 g, 20.9 mmol) was added and the reaction was stirred for 20 h. The solvent was evaporated and purified by normal phase chromatography with DCM/MeOH as solvent to give 6.62 g of a white solid (64%). 1H-NMR (d3-ACN, 300 MHz): δ 9.21 (s, NH), 8.62 (d, 1H, J=2.0 Hz), 8.09 (d, 1H, J=8.4 Hz), 7.63 (d, 1H, J=8.4 Hz), 6.65 (bs, NH), 5.40 (bs, NH), 3.5 (m, 12H), 3.28 (m, 2H), 3.06 (m, 2H), 2.65 (m, 2H), 2.51 (m, 2H), 2.70 (m, 4H), 1.40 (s, 9H). ESI-MS: Calc. $C_{27}H_{40}N_5O_7S+$: m/z 578.7; found m/z 578.4.

N1-(3-(2-(2-(3-aminopropoxy)ethoxy)ethoxy)propyl)-N4-(2-cyanobenzo[d]thiazol-6-yl)succinamide hydrochloride (3)

Compound 2 (6.62 g, 11.5 mmol) was stirred in a 500 mL round bottomed flask with DCM (200 mL) and triisopropylsilane (1 mL). A 4.0 M solution of HCl in dioxane (30 mL, 120 mmol) was added and stirred at room temperature for 3 h. The solvent was evaporated to give 6.4 g of a yellow hygroscopic solid (98%). 1H-NMR (d6-DMSO, 300 MHz): δ 10.62 (s, 1H), 8.74 (d, 1H, J=2.0 Hz), 8.15 (d, 1H, J=8.4 Hz), 7.77 (d, 1H, J=8.4 Hz), 3.4 (m, 16H), 3.28 (m, 2H), 3.08 (m, 2H), 2.80 (m, 2H), 2.61 (m, 2H), 2.41 (m, 2H), 1.80, (m, 2H), 1.60 (m, 2H). ESI-MS: Calc. $C_{22}H_{32}N_5O_5S+$: m/z 478.59; found m/z 478.2.

Immobilized Cyanobenzothiazole-Magnetic Cellulose (4)

Carboxymethyl magnetic cellulose (7.24 g, 30-50 μm, Iontosorb MG CM) was taken up in a 250 mL round bottomed flask with compound 3 (800 mg, 1.53 mmol) in DMF (100 mL). EDAC (387 mg, 2.01 mmol) was added, and the reaction was stirred for 20 h at room temperature. The particles were filtered on a frit and rinsed first with DMF (200 mL) then 25% EtOH (300 mL) and stored as a 50% suspension at 4° C.

B. Synthesis of HALOTAG Protein Paramagnetic Beads

To create the HALOTAG protein paramagnetic beads, HALOTAG protein was immobilized onto the paramagnetic STEP4 resin through an N-terminal cysteine. HALOTAG protein was expressed in *E. coli* as a HisTag-miniGroEL-HALOTAG fusion with a TEV protease recognition site (EDLYFQC) between HALOTAG protein and the miniGroEL sequences. The fusion was purified using HisTag and then cleaved with the TEV protease in the presence of 2 mM TCEP to expose an N-terminal reduced cysteine. The reactive cyano group on the STEP4 resin reacts with the reduced N-terminal cysteine to form a very stable bond resulting with the HALOTAG protein beads.

Example 10

The following example demonstrates the minimal impact of the chloroalkane modification on permeability and potency of the tethered bioactive agent.

Figure 10:
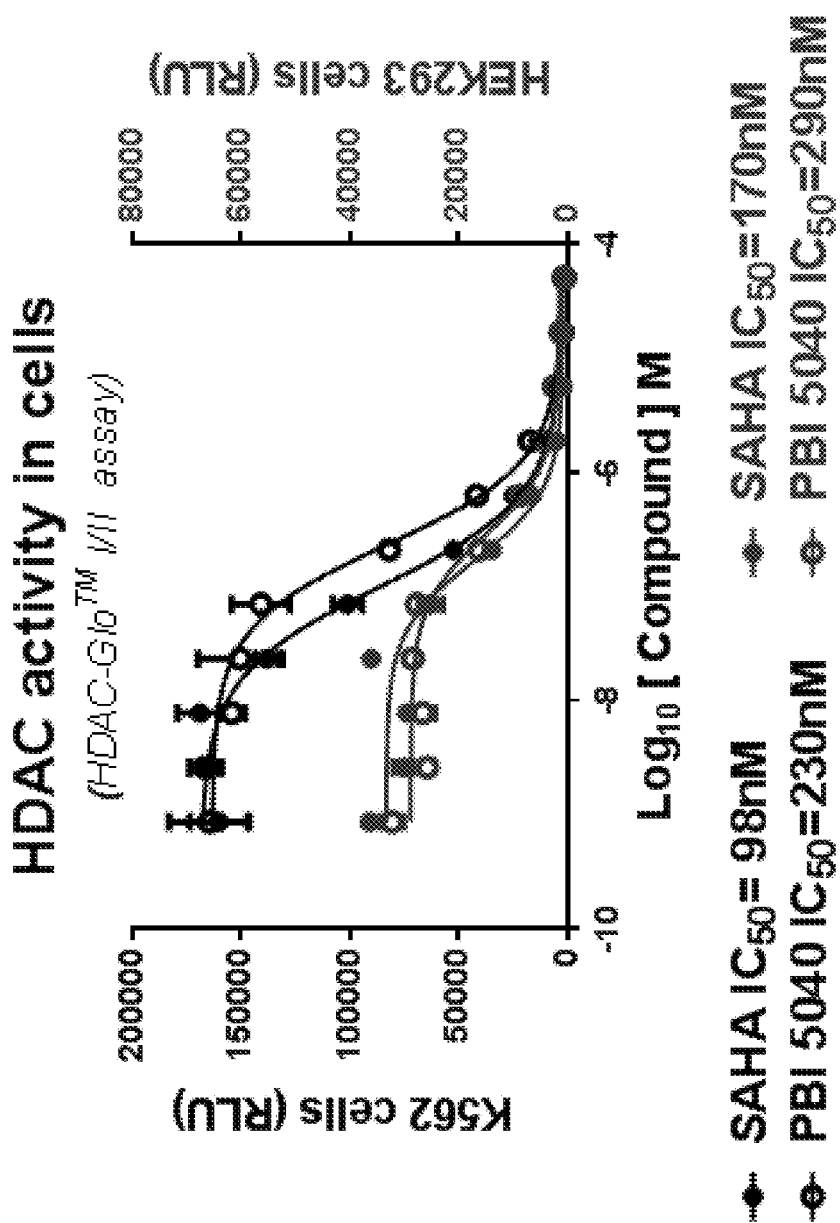
FIG. 10 shows the minimal impact of the chloroalkane modification on permeability and potency of the tethered bioactive agent, SAHA.

HEK293 cells were plated in a 96-well plate at $1\times10^5$ cell/ml in DMEM+10% serum, and 24 hours later, the media was replaced with serum free DMEM media. K562 cells were plated in serum free RPMI 1640 media into wells of a 96-well plate at $2\times10^5$ cells/ml. Cells were treated with serial dilutions of SAHA or PBI-5040 (SAHA-chloroalkane) for 2 hours and then tested for intracellular HDAC activity using the non-lytic HDAC-Glo™ I/II assay (Promega Corporation) according to manufacturer's instructions. The results in FIG. 10 indicate similar inhibition of HDAC activity by SAHA and PBI-5040. The ~2-fold reduction in SAHA potency due to the chloroalkane modification indicates minimal impact of the chloroalkane on cellular permeability or potency.

Example 11

The following example demonstrates the ability of a chloroalkane-conjugated drug to pull-down endogenous targets from cells including low abundance and low affinity targets.

Figure 11:
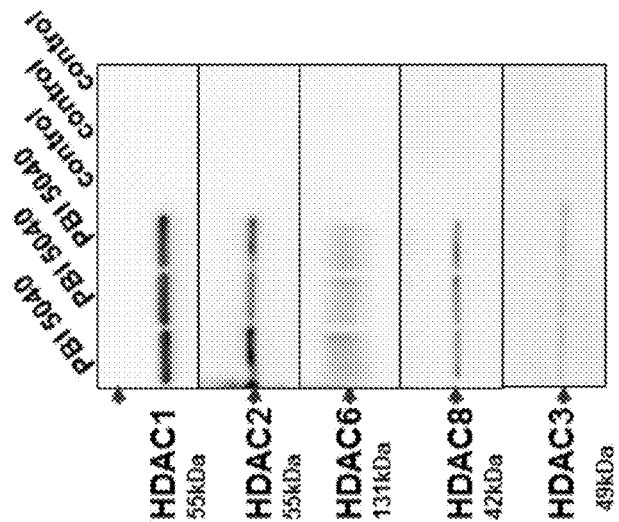
FIG. 11 shows that all known targets of SAHA, including low affinity target (HDAC8) and low abundance target (HDAC3), can be specifically pulled down from the cells using an embodiment of the present invention. (Left) a western blot demonstrating specific pull down of all known targets using SAHA-CA and (right) mass spectrometry analysis of protein pull down by SAHA-CA from HEK293 cells.

HEK293 cells were plated in 100 mm dishes at $2\times10^5$ cells/ml. Forty-eight hours post plating, a final concentration of 20 uM SAHA-chloroalkane (PBI-5040) was added to 3 of the dishes ($1\times10^7$ cells/dish), while 3 other dishes were not treated with the conjugated drug (control). Following equilibrium binding for 2 hours, the media was removed, the cells quickly washed with PBS, lysed in a detergent-based lysis buffer for 10 minutes and centrifuged at 3000×g for 1 minute. The cleared lysates were than added to 75 ul of settled paramagnetic HALOTAG beads and incubated with shaking for 15 minutes. Following binding, the unbound fraction was removed, the HALOTAG paramagnetic beads were washed 3× (wash buffer—50 mM HEPES pH7.5, 150 mM NaCl and 0.01% IGEPAL), and the captured targets specifically released from the beads by competition with 400 μM unconjugated SAHA for 60 minutes. The released targets were subjected to mass spec analysis (FIG. 11B) as well as western blot analysis (FIG. 1-A) with anti HDAC1 antibody (ABCAM); anti HDAC2 antibody (ABCAM); anti HDAC6 antibody (Millipore); anti HDAC3 antibody (Thermo Fisher) and anti HDAC8 antibody (Rockland/Promega). The results in FIG. 11 indicate that all known targets of SAHA, including low affinity target (HDAC8) and low abundance target (HDAC3), can be specifically pull down from the cells using an embodiment of the present invention.

Example 12

The following example demonstrates the effect of the linkage method (chloroalkane or biotin) on drug potency.

Figure 12:
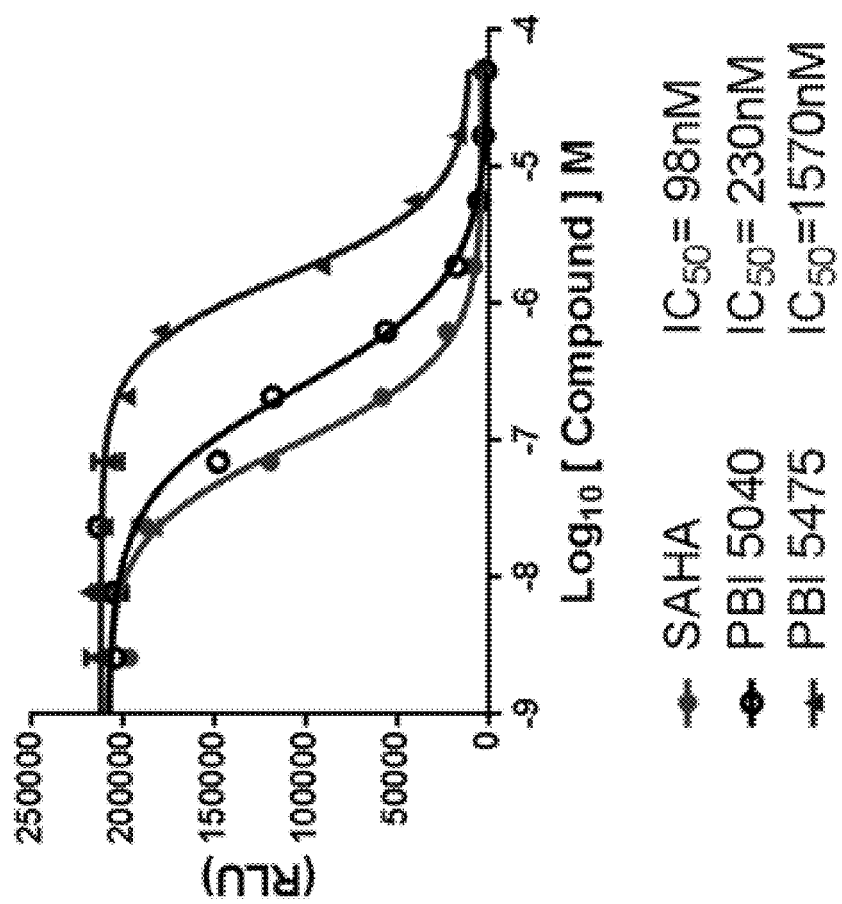
FIG. 12 shows the minimal impact of the chloroalkane modification on permeability and potency of the bioactive agent, SAHA, compared to a biotin modification.

K562 cells were plated in serum free RPMI 1640 media into wells of a 96-well plate at $2\times10^5$ cells/ml. Cells were then treated with serial dilution of SAHA, PBI-5040 (SAHA-chloroalkane) or PBI 5475 (SAHA-biotin) for 2 hours and then tested for intracellular HDAC activity using the non-lytic HDAC-Glo™ I/II assay (Promega Corporation) according to manufacturer's instructions. The results in FIG. 12 indicate a ~2 fold reduction in potency for the chloroalkane modification compared to a ~16 fold reduction in potency for the biotin modification. These results further demonstrate the minimal impact of the chloroalkane linkage on cellular permeability or potency when used with a bioactive agent.

Example 13

The following example demonstrates the highly efficient pull-down mediated by the chloroalkane linkage compared to a biotin linkage in an embodiment of the present invention.

Figure 13:
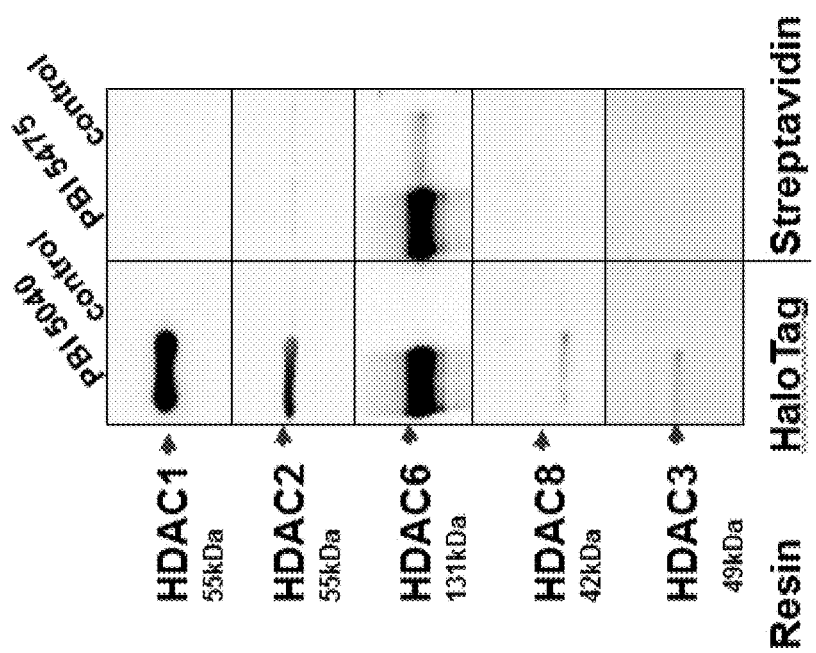
FIG. 13 shows a Western blot demonstrating specific pull down of all known targets of SAHA from K562 cells by SAHA-CA including low affinity target (HDAC8) and low abundance target (HDAC3) while only HDAC6 was pulled down by SAHA-biotin.

K562 cells were plated in 150 mm dishes at 5×10⁷ cells/dish. A final concentration of 20 uM SAHA chloroalkane (PBI-5040) or PBI-5475 (SAHA-biotin) was added to 2 dishes of cells while 2 other dishes of cells were not treated with the conjugated drug (control). Following equilibrium binding of 2 hours, the media was removed, the cells quickly washed with PBS and lysed in detergent-based lysis buffer for 10 minutes and centrifuged at 3000×g for 1 minute. The cleared lysates treated with PBI-5040, as well as the cleared lysates of the control cells, were added to 75 ul of settled paramagnetic HALTOG beads. The cleared lysates of the cells treated with PBI-5475, as well as the cleared lysate of the control cells, were added to 75 ul of settled paramagnetic Streptavidin beads (GE). Following 15 minutes of binding, the unbound fraction was removed, beads were washed 3×, and the captured targets specifically released from the beads by competition with 400 μM unconjugated SAHA for 60 minutes. The released targets were subjected to western blot analysis (FIG. 13) with anti HDAC1 antibody (ABCAM); anti HDAC2 antibody (ABCAM); anti HDAC6 antibody (Millipore); anti HDAC3 antibody (Thermo Fisher) and anti HDAC8 antibody (Rockland/Promega). The results in FIG. 13 indicate that while all known targets of SAHA, including a low affinity target (HDAC8) and a low abundance target (HDAC3), were specifically pulled down by SAHA-chloroalkane, only HDAC6 was pulled down by SAHA-biotin. These results further demonstrate the advantages of the chloroalkane linkage for pull-down of endogenous targets in embodiments of the present invention.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

---

We claim:

1. A composition comprising:
    (a) lysed cells comprising a cellular target of a small molecule bioactive agent;
    (b) the small molecule bioactive agent tethered to a chloroalkane capture ligand, wherein the small molecule bioactive agent is capable of non-covalently binding to the cellular target; and
    (c) a solid surface displaying a dehalogenase capture protein, wherein the dehalogenase capture protein is capable of forming a covalent bond with the chloroalkane capture ligand upon interaction thereof.
2. The composition of claim 1, wherein the cellular target is a fusion with a reporter protein.
3. The composition of claim 2, wherein the reporter protein is a bioluminescent reporter.
4. The composition of claim 3, wherein the bioluminescent reporter comprises a polypeptide with at least 70% sequence identity with SEQ ID NO.: 3.
5. The composition of claim 1, wherein the dehalogenase capture protein comprises at least 70% sequence identity with SEQ ID NO.: 1.
6. The composition of claim 1, wherein the solid surface is selected from the group consisting of well, tube, slide, plate, matrix, resin and bead.
7. The composition of claim 6, wherein the solid surface is magnetic or paramagnetic.
8. The composition of claim 1, wherein the cellular target is bound to the small molecule bioactive agent, and the capture protein is bound to the capture ligand.

* * * * *